US009045791B2

(12) United States Patent
Flechtner et al.

(10) Patent No.: US 9,045,791 B2
(45) Date of Patent: Jun. 2, 2015

(54) ANTIGEN SCREENING SYSTEM

(71) Applicant: GENOCEA BIOSCIENCES, INC., Cambridge, MA (US)

(72) Inventors: Jessica Flechtner, Maynard, MA (US); Todd Gierahn, Brookline, MA (US)

(73) Assignee: Genocea Biosciences, Inc., Cambridge, MA (US)

( * ) Notice: Subject to any disclaimer, the term of this patent is extended or adjusted under 35 U.S.C. 154(b) by 53 days.

(21) Appl. No.: 13/627,332

(22) Filed: Sep. 26, 2012

(65) Prior Publication Data
US 2013/0102496 A1    Apr. 25, 2013

Related U.S. Application Data

(63) Continuation of application No. 12/496,171, filed on Jul. 1, 2009, now Pat. No. 8,313,894.

(60) Provisional application No. 61/077,323, filed on Jul. 1, 2008.

(51) Int. Cl.
*C12Q 1/00* (2006.01)
*C12Q 1/02* (2006.01)
*G01N 33/50* (2006.01)
*G01N 33/569* (2006.01)

(52) U.S. Cl.
CPC ............ *C12Q 1/025* (2013.01); *G01N 33/5047* (2013.01); *G01N 33/569* (2013.01)

(58) Field of Classification Search
CPC .................................................... C12Q 1/025
See application file for complete search history.

(56) References Cited

U.S. PATENT DOCUMENTS

| | | | |
|---|---|---|---|
| 4,863,874 A | 9/1989 | Wassef et al. |
| 4,921,757 A | 5/1990 | Wheatley et al. |
| 4,925,661 A | 5/1990 | Huang |
| 5,199,942 A | 4/1993 | Gillis |
| 5,225,212 A | 7/1993 | Martin et al. |
| 5,510,240 A | 4/1996 | Lam et al. |
| 5,643,599 A | 7/1997 | Lee et al. |
| 5,989,565 A | 11/1999 | Storkus et al. |
| 6,004,815 A | 12/1999 | Portnoy et al. |
| 6,086,898 A | 7/2000 | DeKruyff et al. |
| 6,407,063 B1 | 6/2002 | Luiten et al. |
| 7,262,269 B2 | 8/2007 | Lam et al. |
| 2003/0077263 A1 | 4/2003 | Maraskovsky et al. |
| 2004/0001849 A1 | 1/2004 | Punnonen et al. |
| 2004/0115221 A1 | 6/2004 | Portnoy et al. |
| 2005/0106641 A1 | 5/2005 | Kauvar et al. |
| 2005/0112576 A1 | 5/2005 | Deml |
| 2007/0238182 A1 | 10/2007 | Gaiger et al. |
| 2008/0131871 A1 | 6/2008 | Chen et al. |
| 2010/0260791 A1 | 10/2010 | Higgins et al. |

FOREIGN PATENT DOCUMENTS

EP          1715346 A1    10/2006
WO    WO-2007/098255 A2    8/2007

OTHER PUBLICATIONS

Ayada, K. et al, Chronic Infections and Atherosclerosis, Annals of the New York Academy of Sciences, 1108:594-602 (2007).
Bach, J., Infections and Autoimmune Diseases, Journal of Autoimmunity, 25:74-80 (2005).
Barzilai, O. et al., Viral Infection Can Induce the Production of Autoantibodies, Current Opinion in Rheumatology, 19:636-643 (2007).
Bendtsen, J. D. et al, Improved Prediction of Signal Peptides: SignalP 3.0, Journal of Molecular Biology, 340:783-795 (2004).
Betzner, A.S. and Keck, W., Molecular Cloning, Overexpression and Mapping of the SLT Gene Encoding the Soluble Lytic Transglycosylase of *Escherichia coli*, Molecular Genetics & Genomics, 219:489-491 (1989).
Blommel, P.G. et al., High Efficiency Single Step Production of Expression Plasmids from cDNA Clones Using the Flexi Vector Cloning System, Protein Expression & Purification, 47:562-570 (2006).
Buist, G. et al., Autolysis of *Lactococcus lactis* by Induced Overproduction of its Major Autolysin, AcmA, Applied and Environmental Microbiology, 63(7):2722-2728 (1997).
Cao, P. et al., Extracellular Release of Antigenic Proteins by *Helicobacter pylori*, Infection and Immunity, 66(6):2984-2986 (1998).
Chang, C. et al., S Gene Expression and the Timing of Lysis by Bacteriophage λ, Journal of Bacteriology, 177(11):3283-3294 (1995).
Courvalin, P. et al., Gene Transfer from Bacteria to Mammalian Cells, Comptes Rendus de l'Academie des Sciences, 318:1207-1212 (1995).
Drouin, E.E. et al., Human Homologues of a Borrelia T Cell Epitope Associated with Antibiotic-Refractory Lyme Arthritis, Molecular Immunology, 45(1):180-189 (2008).
Falk, K. et al., Allele-Specific Motifs Revealed by Sequencing of Self-Peptides Eluted from MHC Molecules. Nature, 351(6324):290-296 (1991).
Goodall, J.C. et al, Identification of *Chlamydia trachomatis* Antigens Recognized by Human CD4+ T Lymphocytes by Screening an Expression Library. European Journal of Immunology, 31:1513-1522 (2001).
Higgins, D.E. et al, Delivery of Protein to the Cytosol of Macrophages using *Escherichia coli* K-12, Molecular Microbiology, 31(6):1631-1641 (1999).
Inaba, K. et al, Isolation of Dendritic Cells, Current Protocols in Immunology, 3(3.7):1-15 (1998).
International Search Report for PCT/US2009/049406, 3 pages (Oct. 13, 2009).
Isberg, R.R. et al, Identification of Invasin: A Protein that Allows Enteric Bacteria to Penetrate Cultured Mammalian Cells, Cell. 50:769-778 (1987).
Jensen, R.B. and Gerdes, K., Programmed Cell Death in Bacteria: Proteic Plasmid Stabilization Systems, Molecular Microbiology, 17(2):205-210 (1995).

(Continued)

*Primary Examiner* — Albert Navarro

(74) *Attorney, Agent, or Firm* — Choate, Hall & Stewart, LLP; Brenda Herschbach Jarrell; Rolando Medina

(57) ABSTRACT

Methods and compositions for identifying antigens of human lymphocytes are provided herein.

23 Claims, 1 Drawing Sheet

(56) References Cited

OTHER PUBLICATIONS

Lam, K.S. et al, A New Type of Synthetic Peptide Library for Identifying Ligand-Binding Activity, Nature, 354:82-84 (1991).

Liolios, K. et al., The Genomes On Line Database (GOLD) v.2: A Monitor of Genome Projects Worldwide. Nucleic Acids Research, 34:1-3 (2006).

Lubitz, W. et al., Requirement for a Functional Host Cell Autolytic Enzyme System for Lysis of *Escherichia coli* by Bacteriophage φX174, Journal of Bacteriology, 159(1):385-387 (1984).

Manguson, R. et al., Autoregulation of the Plasmid Addiction Operon of Bacteriophage P1, The Journal of Biological Chemistry, 21(31):18705-18710 (1996).

Margot, P. et al., The LytE Gene of *Bacillus subtilis* 168 Encodes a Cell Wall Hydrolase, Journal of Bacteriology, 180(3):749-752 (1998).

Marsischky, G. and Labaer, J., Many Paths to Many Clones: A Comparative Look at High-Throughput Cloning Methods, Genome Research, 14:2020-2028 (2004).

Raab, R. et al., Dominance in Lambda S Mutations and Evidence for Translational Control, Journal of Molecular Biology, 199:95-105 (1988).

Romero, A. et al., Lytic Action of Cloned Pneumococcal Phase Lysis Genes in *Streptococcus pneumoniae*, FEMS Microbiology Letters, 108:87-92 (1993).

Sanderson, S. et al., Identification of a CDF+ T Cell-Stimulating Antigen of Pathogenic Bacteria by Expression Cloning, Journal of Experimental Medicine, 182(6):1751-1757 (1995).

Sizemore, D.R. et al., Attenuated Shigella as a DNA Delivery Vehicle for DNA-Mediated Immunication. Science, 270:209-302 (1995).

Smith, A.S.G. and Rawlings, D.E., The Poison-Antidote Stability System of the Broad-Host-Rage *Thiobacillus ferrooxidans* Plasmid pTF-FC2, Molecular Microbiology, 26(5)961-970 (1997).

Tomasz, A. et al., Insertional Inactivation of the Major Autolysin Gene of *Streptococcus pneumoniae*. Journal of Bacteriology, 170(12):5931-5934 (1998).

Walhout, A.J.M. et al., GATEWAY Recombinational Cloning: Application to the Cloning of Large Numbers of Open Reading Frames or ORFeomes, Methods in Enzymology, 328:575-592 (2000).

Written Opinion for PCT/US2009/049406, 7 pages (Oct. 13, 2009).

Yamanaka, K. et al., Characterization of *Bacillus subtilis* Mutants Resistant to Cold Shock-Induced Autolysis. FEMS Microbiology Letters, 150:269-275 (1997).

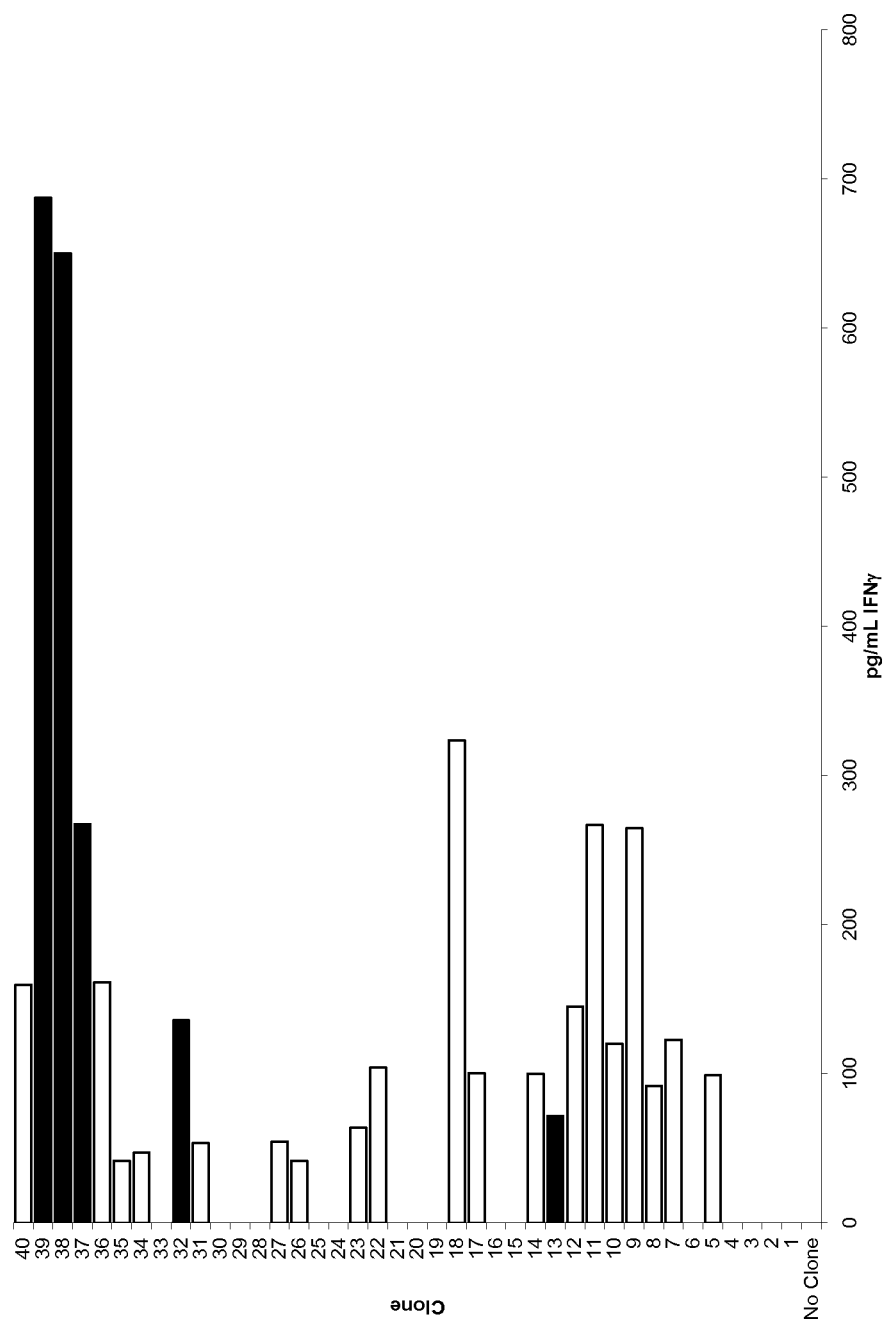

US 9,045,791 B2

ANTIGEN SCREENING SYSTEM

CROSS REFERENCE TO RELATED APPLICATIONS

The present application is continuation of U.S. patent application Ser. No. 12/496,171, filed Jul. 1, 2009, which claims the benefit of U.S. Provisional Patent Application Ser. No. to U.S. 61/077,323, filed Jul. 1, 2008; the entire contents of which are incorporated herein by reference.

SEQUENCE LISTING

In accordance with 37 CFR 1.52(e)(5), the Sequence Listing submitted in the form of an ASCII text file (entitled "Sequence_Listing.txt" created on Dec. 21, 2012, and 20 kilobytes in size) is incorporated herein by reference in its entirety.

BACKGROUND OF THE INVENTION

Despite advances in vaccine development and antimicrobial therapies, infectious diseases remain widespread. Nationwide, at least 45 million people ages 12 and older, or one out of five adolescents and adults, have had genital Herpes infection. The prevalence of herpes simplex virus-2 (HSV-2) is increasing worldwide and there is now evidence linking it to HIV transmission. HIV has infected 40 million people to date and causes 2-3 million deaths each year (Joint United Nations Programme on HIV/AIDS, 2006 Report on the Global AIDS Epidemic, Ch. 2, 2006). Nine million new cases of tuberculosis were reported in 2005, with 1.6 million deaths in that year alone (Young et al., *Clin Invest.* 118(4): 1255-1265, 2008). Malaria causes disease in hundreds of millions and kills 1-3 million each year (Snow et al., *Nature* 434 (7030):214-7, 2005). Efforts to limit the spread of these and other pathogens and control their devastating effects on human populations require effective vaccines. There remains a need for improved vaccines, and for systems to develop them.

The efficacy of many current vaccines lies in their ability to elicit robust antibody responses. However, T cell mediated immunity is important for protection from many types of infections, including those for which no effective vaccine is available. $CD4^+$ T cells orchestrate humoral and cell mediated immune responses in vivo. $CD8^+$ T cells are critical for the control of intracellular pathogens. Identifying antigens that elicit T cell mediated responses has been more technically laborious than characterizing humoral antigens.

SUMMARY OF THE INVENTION

The present invention features, inter alia, methods of identifying antigens of human lymphocytes as well as compositions including the antigens and methods of using the antigens. The invention also features methods of evaluating an immune response in a human subject, e.g., for diagnostic applications.

Accordingly, in certain embodiments, the present invention provides methods of identifying antigens. In certain embodiments, methods include (a) providing a library of cells (e.g., bacterial cells), wherein each cell of the library includes a heterologous polypeptide; (b) contacting the cells with a first plurality of human cells which comprises human antigen presenting cells that internalize library cells; (c) contacting the first plurality of human cells with a second plurality of human cells, which second plurality includes human lymphocytes (e.g., T cells, such as $CD4^+$ T cells, $CD8^+$ T cells), under conditions in which the lymphocytes are stimulated by polypeptides presented by the first plurality of human cells; and (d) determining whether a lymphocyte of the second plurality of human cells is stimulated by a heterologous polypeptide presented by a cell of the first plurality of human cells. Stimulation of a lymphocyte by a heterologous polypeptide indicates that the heterologous polypeptide is an antigen.

In some embodiments, library cells include a cytolysin polypeptide, such as listeriolysin O (LLO). In some embodiments, cells of the first and second plurality include primary cells (e.g., primary peripheral blood mononuclear cells (PBMC)). In some embodiments, cells of the first and second plurality include cells from the same individual. In some embodiments, the individual is an individual that has been exposed to an infectious agent, and the heterologous polypeptides are polypeptides encoded by the infectious agent or a related species thereof. In some embodiments, the individual is an individual that has or had a cancer, or an autoimmune disease.

The details of one or more embodiments of the invention are set forth in the accompanying drawings and the description below. Other features, objects, and advantages of the invention will be apparent from the description and drawing, and from the claims. All cited patents, and patent applications and references (including references to public sequence database entries) are incorporated by reference in their entireties for all purposes.

BRIEF DESCRIPTION OF THE DRAWING

FIG. 1 is a graph showing IFNγ secreted in supernatants by human $CD8^+$ T cells cocultured with autologous antigen presenting cells pulsed with *E. coli* expressing cytoplasmic listeriolysin O and polypeptides encoded by herpes simplex virus-2 (HSV-2) (single viral clones). Each bar represents IFNγ levels secreted by T cells exposed to antigen presenting cells that had internalized library cells expressing a single viral polypeptide. Black bars represent clones that had also been previously identified by other methods.

DEFINITIONS

Antigen: The term "antigen", as used herein, refers to a molecule (e.g., a polypeptide) that elicits a specific immune response. Antigen specific immunological responses, also known as adaptive immune responses, are mediated by lymphocytes (e.g., T cells, B cells) that express antigen receptors (e.g., T cell receptors, B cell receptors). In certain embodiments, an antigen is a T cell antigen, and elicits a cellular immune response. In certain embodiments, an antigen is a B cell antigen, and elicits a humoral (i.e., antibody) response. In certain embodiments, an antigen is both a T cell antigen and a B cell antigen. As used herein, the term "antigen" encompasses both a full length polypeptide as well as a portion of the polypeptide, and a peptide epitope within the polypeptides (e.g., a peptide epitope bound by a Major Histocompatibility Complex (MHC) molecule (e.g., MHC class I, or MHC class II).

Antigen presenting cell: An "antigen presenting cell" or "APC" refers to a cell that presents peptides on MHC class I and/or MHC class II molecules. APC include both professional APC (e.g., dendritic cells, macrophages, B cells), which have the ability to stimulate naïve lymphocytes, and non-professional APC (e.g., fibroblasts, epithelial cells, endothelial cells, glial cells). In certain embodiments, APC are able to internalize (e.g., endocytose) members of a library (e.g., cells of a library of bacterial cells) that express heterologous polypeptides as candidate antigens.

Autolysin polypeptide: An "autolysin polypeptide" is a polypeptide that facilitates or mediates autolysis of a cell (e.g., a bacterial cell) that has been internalized by a eukaryotic cell. In some embodiments, an autolysin polypeptide is a bacterial autolysin polypeptide. Autolysin polypeptides include, and are not limited to, polypeptides whose sequences are disclosed in GenBank® under Acc. Nos. NP_388823.1, NP_266427.1, and P0AGC3.1.

Cytolysin polypeptide: A "cytolysin polypeptide" is a polypeptide that has the ability to form pores in a membrane of a eukaryotic cell. A cytolysin polypeptide, when expressed in host cell (e.g., a bacterial cell) that has been internalized by a eukaryotic cell, facilitates release of host cell components (e.g., host cell macromolecules, such as host cell polypeptides) into the cytosol of the internalizing cell. In some embodiments, a cytolysin polypeptide is bacterial cytolysin polypeptide. In some embodiments, a cytolysin polypeptide is a cytoplasmic cytolysin polypeptide. Cytolysin polypeptides include, and are not limited to, polypeptides whose sequences are disclosed in U.S. Pat. No. 6,004,815, and in GenBank® under Acc. Nos. NP_463733.1, NP_979614, NP_834769, YP_084586, YP_895748, YP_694620, YP_012823, NP_346351, YP_597752, BAB41212.2, NP_561079.1, and YP_001198769.

Cytoplasmic cytolysin polypeptide: A "cytoplasmic cytolysin polypeptide" is a cytolysin polypeptide that has the ability to form pores in a membrane of a eukaryotic cell, and that is expressed as a cytoplasmic polypeptide in a bacterial cell. A cytoplasmic cytolysin polypeptide is not significantly secreted by a bacterial cell. Cytoplasmic cytolysin polypeptides can be provided by a variety of means. In some embodiments, a cytoplasmic cytolysin polypeptide has a sequence that is altered relative to the sequence of a secreted cytolysin polypeptide (e.g., altered by deletion or alteration of a signal sequence to render it nonfunctional). In some embodiments, a cytoplasmic cytolysin polypeptide is cytoplasmic because it is expressed in a secretion-incompetent cell. In some embodiments, a cytoplasmic cytolysin polypeptide is cytoplasmic because it is expressed in a cell that does not recognize and mediate secretion of a signal sequence linked to the cytolysin polypeptide. In some embodiments, a cytoplasmic cytolysin polypeptide is a bacterial cytolysin polypeptide.

Heterologous: The term "heterologous", as used herein to refer to genes or polypeptides, refers to a gene or polypeptide that does not naturally occur in the organism in which it is present and/or being expressed, and/or that has been introduced into the organism by the hand of man. Heterologous polypeptides used in accordance with the present invention are typically polypeptides from infectious agents. In some embodiments, a heterologous polypeptide expressed in a bacterial host cell is a polypeptide encoded by a bacterial species that is different from the bacterial host cell species. In some embodiments, a heterologous polypeptide expressed in a bacterial host cell is a polypeptide encoded by a virus. Where a plurality of different heterologous polypeptides are to be introduced into and/or expressed by cells (e.g., a library of cells), the different polypeptides may all be from the same infectious agent (e.g., from a single bacterial or viral species). In some embodiments, the different polypeptides are from more than one infectious agent (e.g., from two bacterial species, two viral species, or a bacterial species and a viral species). In some embodiments, the plurality of different polypeptides represents polypeptides from a complete set of open reading frames (ORFs) expressed by an infectious agent.

Invasin polypeptide: An "invasin polypeptide" is a polypeptide that facilitates or mediates uptake of a cell (e.g., a bacterial cell) by a eukaryotic cell. Expression of an invasin polypeptide in a noninvasive bacterial cell confers on the cell the ability to enter a eukaryotic cell. In some embodiments, an invasin polypeptide is a bacterial invasin polypeptide. In some embodiments, an invasin polypeptide is a *Yersinia* invasin polypeptide (e.g., a *Yersinia* invasin polypeptide comprising a sequence disclosed in GenBank® under Acc. No. YP_070195.1).

Listeriolysin O (LLO): The terms "listeriolysin O" or "LLO" refer to a listeriolysin O polypeptide of *Listeria monocytogenes* and truncated forms thereof that retain pore-forming ability (e.g., cytoplasmic forms of LLO, including truncated forms lacking a signal sequence). In some embodiments, an LLO is a cytoplasmic LLO. Exemplary LLO sequences are shown in Table 1, below.

Polypeptide: The term "polypeptide", as used herein, generally has its art-recognized meaning of a polymer of at least three amino acids. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides.

Primary cells: As used herein, "primary cells" refers to cells from an organism that have not been immortalized in vitro. In some embodiments, primary cells are cells taken directly from a subject (e.g., a human). In some embodiments, primary cells are progeny of cells taken from a subject (e.g., cells that have been passaged in vitro). Primary cells include cells that have been stimulated to proliferate in culture.

Related species: As used herein, a species is "related" to another species if it is in the same family or genus and/or if antigens from the species elicit a cross-reactive immune response in an individual. In some embodiments, cells from an individual that has been exposed to an infectious agent are used to identify an antigen from the infectious agent or a related species thereof. For example, cells from an individual that has been exposed to a first herpesvirus species can be screened against cells expressing candidate antigens from the first herpesvirus species, or a second, related herpesvirus species.

Stimulate: As used herein, a peptide presented by an antigen presenting cell "stimulates" a lymphocyte if the lymphocyte is detectably activated after exposure to the peptide/APC under conditions that permit antigen specific recognition to occur. Any indicator of lymphocyte activation can be evaluated to determine whether a lymphocyte is stimulated (e.g., proliferation, cytokine secretion, change in expression of one or more activation markers).

DETAILED DESCRIPTION OF CERTAIN EMBODIMENTS OF THE INVENTION

The present invention provides systems for the rapid identification of antigens that elicit T cell immunity, and particularly that elicit human T cell immunity. The present invention allows analysis of complete proteomes of infectious agents, and is particularly powerful now that complete genomes are available for hundreds of such infectious agents. The present invention therefore solves the ultimate challenge in vaccine development: identification of antigens that elicit T cell immunity in humans.

Library Generation

A library is a collection of members (e.g., cells or non-cellular particles, such as virus particles, liposomes, or beads (e.g., beads coated with polypeptides, such as in vitro translated polypeptides, e.g., affinity beads, e.g., antibody coated beads, or NTA-Ni beads bound to polypeptides of interest). According to the present invention, members of a library include (e.g., internally express) heterologous polypeptides. In some embodiments, members of a library which are cells internally express heterologous polypeptides. In some embodiments, members of a library which are particles include internally, and/or are bound to, heterologous polypeptides. Use of a library in an assay system allows simultaneous evaluation in vitro of cellular responses to multiple candidate antigens. Members of the library are constructed to include (e.g., internally express) heterologous polypeptides from an infectious agent or target cell of interest (e.g., a tumor cell, or a cell which is a target of an autoimmune response). According to the present invention, a library is designed to be internalized by human antigen presenting cells so that peptides from library members, including peptides from internally expressed heterologous polypeptides, are presented on MHC molecules of the antigen presenting cells for recognition by T cells.

Libraries can be used in assays that detect peptides presented by human MHC class I and MHC class II molecules. Polypeptides expressed by the internalized library members are digested in intracellular endocytic compartments (e.g., phagosomes, endosomes, lysosomes) of the human cells and presented on MHC class II molecules, which are recognized by human CD4$^+$ T cells. In some embodiments, library members include a cytolysin polypeptide, in addition to the heterologous polypeptide. In some embodiments, library members include an invasin polypeptide, in addition to the heterologous polypeptide. In some embodiments, library members include an autolysin polypeptide, in addition to the heterologous polypeptide. In some embodiments, library members are provided with cells that express a cytolysin polypeptide (i.e., the cytolysin and heterologous polypeptide are not expressed in the same cell, and an antigen presenting cell is exposed to members that include the cytolysin and members that include the heterologous polypeptide, such that the antigen presenting cell internalizes both, and such that the cytolysin facilitates delivery of heterologous polypeptides to the MHC class I pathway of the antigen presenting cell). A cytolysin polypeptide can be constituitively expressed in a cell, or it can be under the control of an inducible expression system (e.g., an inducible promoter). In some embodiments, a cytolysin is expressed under the control of an inducible promoter to minimize cytotoxicity to the cell that expresses the cytolysin.

Once internalized by a human cell, a cytolysin polypeptide perforates intracellular compartments in the human cell, allowing polypeptides expressed by the library members to gain access to the cytosol of the human cell. Polypeptides released into the cytosol are presented on MHC class I molecules, which are recognized by CD8$^+$ T cells.

A library can be comprised of any type of cell or particle that can be internalized by, and deliver a heterologous polypeptide (and a cytolysin polypeptide, in applications where a cytolysin polypeptide is desirable) to, antigen presenting cells for use in methods described herein. Although the term "cell" is used throughout the present specification to refer to a library member, it is understood that, in some embodiments, the library member is a non-cellular particle, such as a virus particle, liposome, or bead. In some embodiments, members of the library include polynucleotides that encode the heterologous polypeptide (and cytolysin polypeptide), and can be induced to express the heterologous polypeptide (and cytolysin polypeptide) prior to, and/or during internalization by antigen presenting cells. In some embodiments, members of the library include bacterial cells. In certain embodiments, the library includes nonpathogenic, nonvirulent bacterial cells. Examples of bacteria for use as library members include *E. coli*, mycobacteria, *Listeria monocytogenes*, *Shigella flexneri*, *Bacillus subtilis*, or *Salmonella*.

In some embodiments, members of the library include eukaryotic cells (e.g., yeast cells). In some embodiments, members of the library include viruses (e.g., bacteriophages). In some embodiments, members of the library include liposomes. Methods for preparing liposomes that include a cytolysin and other agents are described in Kyung-Dall et al., U.S. Pat. No. 5,643,599. In some embodiments, members of the library include beads. Methods for preparing libraries comprised of beads are described, e.g., in Lam et al., *Nature* 354: 82-84, 1991, U.S. Pat. Nos. 5,510,240 and 7,262,269, and references cited therein.

In certain embodiments, a library is constructed by cloning polynucleotides encoding open reading frames of an infectious agent or target cell, or portions thereof, into vectors that express the ORFs in cells of the library. The polynucleotides can be cloned by designing primers that amplify the ORFs. Primers can be designed using available software, such as Primer3Plus (available the following URL: bioinformatics.nl/cgi-bin/primer3plus/primer3plus.cgi; see Rozen and Skaletsky, In: Krawetz S, Misener S (eds) *Bioinformatics Methods and Protocols: Methods in Molecular Biology*. Humana Press, Totowa, N.J., pp. 365-386, 2000). Other methods for designing primers are known to those of skill in the art. In some embodiments, primers are constructed so as to produce polypeptides that are truncated, and/or lack hydrophobic regions (e.g., signal sequences or transmembrane regions) to promote efficient expression. The location of predicted signal sequences and predicted signal sequence cleavage sites in a given ORF sequence can be determined using available software, see, e.g., Dyrløv et al., *J. Mol. Biol.*, 340: 783-795, 2004, and the following URL: cbs.dtu.dk/services/SignalP/). For example, if a signal sequence is predicted to occur at the N-terminal 20 amino acids of a given polypeptide sequence, a primer is designed to anneal to a coding sequence downstream of the nucleotides encoding the N-terminal 20 amino acids, such that the amplified sequence encodes a product lacking this signal sequence.

Primers can also be designed to include sequences that facilitate subsequent cloning steps. ORFs can be amplified directly from genomic DNA (e.g., genomic DNA of an infectious agent), or from polynucleotides produced by reverse transcription (RT-PCR) of mRNAs expressed by the infectious agent. RT-PCR of mRNA is useful, e.g., when the genomic sequence of interest contains intronic regions. PCR-amplified ORFs are cloned into an appropriate vector, and size, sequence, and expression of ORFs can be verified prior to use in immunological assays.

In some embodiments, an ORF sequence is linked to a sequence encoding a tag (e.g., an N-terminal or C-terminal epitope tag). Epitope tags facilitate purification of expressed ORFs, and can allow one to verify that a given ORF is properly expressed in a library host cell, e.g., prior to using the cell in a screen. Useful epitope tags include, for example, a polyhistidine (His) tag, a V5 epitope tag from the P and V protein of paramyxovirus, a hemagglutinin (HA) tag, a myc tag, and others. In some embodiments, an ORF sequence is fused to a sequence encoding a tag which is a known antigenic epitope (e.g., an MHC class I- and/or MHC class II-restricted T cell epitope of a model antigen such as an ovalbumin), and which can be used to verify that an ORF sequence is expressed and that the ORF-tag fusion polypeptide is processed and presented in antigen presentation assays. In some embodiments a tag includes a T cell epitope of a murine T cell (e.g., a murine T cell line). In some embodiments, an ORF sequence is linked to a tag that facilitates purification and a tag that is a known antigenic epitope.

Polynucleotides encoding the ORFs are cloned into an expression vector for introduction into library host cells. Various vector systems are available to facilitate cloning and manipulation of ORFs, such as the Gateway® Cloning system (Invitrogen). As is known to those of skill in the art, ORF expression vectors include elements that drive production of polypeptides encoded by the ORF in library host cells (e.g., promoter and other regulatory elements). In some embodiments, ORF expression is controlled by an inducible element (e.g., an inducible promoter, e.g., an IPTG- or arabinose-inducible promoter, or an IPTG-inducible phage T7 RNA polymerase system, a lactose (lac) promoter, a tryptophan (trp) promoter, a tac promoter, a trc promoter, a phage lambda promoter, an alkaline phosphatase (phoA) promoter, to give just a few examples; see Cantrell, *Meth. in Mol. Biol.,* 235: 257-276, Humana Press, Casali and Preston, Eds.). In some embodiments, ORFs are expressed as cytoplasmic polypeptides. In some embodiments, the vector used for ORF expression is a vector that has a high copy number in a library host cell. In some embodiments, the vector used for expression has a copy number that is more than 25, 50, 75, 100, 150, 200, or 250 copies per cell. In some embodiments, the vector used for expression has a ColE1 origin of replication. Useful vectors for polypeptide expression in bacteria include pET vectors (Novagen), Gateway® pDEST vectors (Invitrogen), pGEX vectors (Amersham Biosciences), pPRO vectors (BD Biosciences), pBAD vectors (Invitrogen), pLEX vectors (Invitrogen), pMAL™ vectors (New England BioLabs), pGEMEX vectors (Promega), and pQE vectors (Qiagen). Vector systems for producing phage libraries are known and include Novagen T7Select® vectors, and New England Biolabs Ph.D.™ Peptide Display Cloning System.

In some embodiments, library host cells express (either constituitively, or when induced, depending on the selected expression system) an ORF to at least 10%, 20%, 30%, 40%, 50%, 60%, or 70% of the total cellular protein. In some embodiments, the level of expression of an ORF in a library member (e.g., cell, virus particle, liposome, bead) is such that antigen presenting cells exposed to a sufficient quantity of the library members present on MHC molecules ORF epitopes at a density that is comparable to the density presented by antigen presenting cells pulsed with purified peptides.

Methods for efficient, large-scale production of ORF libraries are available. For example, site-specific recombinases or rare-cutting restriction enzymes can be used to transfer ORFs between expression vectors in the proper orientation and reading frame (Walhout et al., *Meth. Enzymol.* 328: 575-592, 2000; Marsischky et al., *Genome Res.* 14:2020-202, 2004; Blommel et al., *Protein Expr. Purif.* 47:562-570, 2006).

For production of liposome libraries, expressed polypeptides (e.g., purified or partially purified polypeptides) can be entrapped in liposomal membranes, e.g., as described in Wassef et al., U.S. Pat. No. 4,863,874; Wheatley et al., U.S. Pat. No. 4,921,757; Huang et al., U.S. Pat. No. 4,925,661; or Martin et al., U.S. Pat. No. 5,225,212.

A library can be designed to include full length polypeptides and/or portions of polypeptides encoded by an infectious agent or target cell. Expression of full length polypeptides maximizes epitopes available for presentation by a human antigen presenting cell, thereby increasing the likelihood of identifying an antigen. However, in some embodiments, it is useful to express portions of ORFs, or ORFs that are otherwise altered, to achieve efficient expression. For example, in some embodiments, ORFs encoding polypeptides that are large (e.g., greater than 1,000 amino acids), that have extended hydrophobic regions, signal peptides, transmembrane domains, or domains that cause cellular toxicity, are modified (e.g., by C-terminal truncation, N-terminal truncation, or internal deletion) to reduce cytotoxicity and permit efficient expression a library cell, which in turn facilitates presentation of the encoded polypeptides on human cells. Other types of modifications, such as point mutations or codon optimization, may also be used to enhance expression.

The number of polypeptides included in a library can be varied. A library can be designed to express polypeptides from at least 5%, 10%, 15%, 20%, 25%, 35%, 40%, 45%, 50%, 55%, 60%, 70%, 75%, 80%, 85%, 90%, 95%, 97%, 98%, 99%, or more, of the ORFs in an infectious agent or target cell. In some embodiments, a library expresses at least 25, 50, 75, 100, 150, 200, 250, 300, 350, 400, 450, 500, 550, 600, 650, 700, 750, 800, 850, 900, 950, or 1000 different heterologous polypeptides, each of which may represent a polypeptide encoded by a single full length ORF or portion thereof.

In some embodiments, it is advantageous to include polypeptides from as many ORFs as possible, to maximize the number of candidate antigens for screening. In some embodiments, a subset of polypeptides having a particular feature of interest is expressed. For example, for assays focused on identifying antigens associated with a particular stage of infection, one can construct a library that expresses a subset of polypeptides associated with that stage of infection (e.g., a library that expresses polypeptides associated with the hepatocyte phase of infection by *Plasmodium falciparum*, e.g., a library that expresses polypeptides associated with a yeast or mold stage of a dimorphic fungal pathogen). In some embodiments, assays may focus on identifying antigens that are secreted polypeptides, cell surface-expressed polypeptides, or virulence determinants, e.g., to identify antigens that are likely to be targets of both humoral and cell mediated immune responses.

In addition to heterologous polypeptides, libraries can include tags that allow one to easily purify, analyze, or evaluate MHC presentation, of the heterologous polypeptide. In some embodiments, ORFs expressed by a library include C-terminal tags that include both an MHC class I and an MHC class II-restricted T cell epitope from a model antigen, such as chicken ovalbumin (OVA). Library protein expression and MHC presentation is validated using these epitopes. In some embodiments, the epitopes are OVA$_{247-265}$ and OVA$_{258-265}$ respectfully, corresponding to positions in the amino acid sequence found in GenBank® under Acc. No. NP_990483. Expression and presentation of linked ORFs can be verified with antigen presentation assays using T cell hybridomas (e.g., B3Z T hybridoma cells, which are H2-K$^b$ restricted, and KZO T hybridoma cells, which are H2-A$^k$ restricted) that specifically recognize these epitopes (see Example 3, below).

Methods and compositions described herein can be used to identify and detect responses to antigens for any agent that infects humans. For example, libraries can be designed to express polypeptides encoded by viruses, bacteria, fungi, protozoa, or helminths that infect humans.

In some embodiments, members of a library include polynucleotides that encode polypeptides from a virus. For example, a library can be designed to express polypeptides from one of the following viruses: an immunodeficiency virus (e.g., a human immunodeficiency virus (HIV), e.g., HIV-1, HIV-2), a hepatitis virus (e.g., hepatitis B virus (HBV), hepatitis C virus (HCV), hepatitis A virus, non-A and non-B hepatitis virus), a herpes virus (e.g., herpes simplex virus type I (HSV-1), HSV-2, Varicella-zoster virus, Epstein Barr virus, human cytomegalovirus, human herpesvirus 6 (HHV-6), HHV-7, HHV-8), a poxvirus (e.g., variola, vaccinia, monkeypox, Molluscum contagiosum virus), an influenza virus, a human papilloma virus, adenovirus, rhinovirus, coronavirus, respiratory syncytial virus, rabies virus, coxsackie virus, human T-cell leukemia virus (types I, II and III), parainfluenza virus, paramyxovirus, poliovirus, rotavirus, rhinovirus, rubella virus, measles virus, mumps virus, adenovirus, yellow fever virus, Norwalk virus, West Nile virus, a Dengue virus, Severe Acute Respiratory Syndrome Coronavirus (SARS-CoV), bunyavirus, Ebola virus, Marburg virus, Eastern equine encephalitis virus, Venezuelan equine encephalitis virus, Japanese encephalitis virus, St. Louis encephalitis virus, Junin virus, Lassa virus, and Lymphocytic choriomeningitis virus. Libraries for other viruses can also be produced and used according to methods described herein.

In some embodiments, members of a library include polynucleotides that encode polypeptides from bacteria (e.g., from a bacterial pathogen). In some embodiments, the bacterial pathogen is an intracellular pathogen. In some embodiments, the bacterial pathogen is an extracellular pathogen. Examples of bacterial pathogens include bacteria from the following genera and species: *Chlamydia* (e.g., *Chlamydia pneumoniae, Chlamydia psittaci, Chlamydia trachomatis*), *Legionella* (e.g., *Legionella pneumophila*), *Listeria* (e.g., *Listeria monocytogenes*), *Rickettsia* (e.g., *R. australis, R. rickettsii, R. akari, R. conorii, R. sibirica, R. japonica, R. africae, R. typhi, R. prowazekii*), *Actinobacter* (e.g., *Actinobacter baumannii*), *Bordetella* (e.g., *Bordetella pertussis*), *Bacillus* (e.g., *Bacillus anthracis, Bacillus cereus*), *Bacteroides* (e.g., *Bacteroides fragilis*), *Bartonella* (e.g., *Bartonella henselae*), *Borrelia* (e.g., *Borrelia burgdorferi*), *Brucella* (e.g., *Brucella abortus, Brucella canis, Brucella melitensis, Brucella suis*), *Campylobacter* (e.g., *Campylobacter jejuni*), *Clostridium* (e.g., *Clostridium botulinum, Clostridium difficile, Clostridium perfringens, Clostridium tetani*), *Corynebacterium* (e.g., *Corynebacterium diphtheriae, Corynebacterium amycolatum*), *Enterococcus* (e.g., *Enterococcus faecalis, Enterococcus faecium*), *Escherichia* (e.g., *Escherichia coli*), *Francisella* (e.g., *Francisella tularensis*), *Haemophilus* (e.g., *Haemophilus influenzae*), *Helicobacter* (e.g., *Helicobacter pylori*), *Klebsiella* (e.g., *Klebsiella pneumoniae*), *Leptospira* (e.g., *Leptospira interrogans*), *Mycobacteria* (e.g., *Mycobacterium leprae, Mycobacterium tuberculosis*), *Mycoplasma* (e.g., *Mycoplasma pneumoniae*), *Neisseria* (e.g., *Neisseria gonorrhoeae, Neisseria meningitidis*), *Pseudomonas* (e.g., *Pseudomonas aeruginosa*), *Salmonella* (e.g., *Salmonella typhi, Salmonella typhimurium, Salmonella enterica*), *Shigella* (e.g., *Shigella dysenteriae, Shigella sonnei*), *Staphylococcus* (e.g., *Staphylococcus aureus, Staphylococcus epidermidis, Staphylococcus saprophyticus*), *Streptococcus* (e.g., *Streptococcus agalactiae, Streptococcus pneumoniae, Streptococcus pyogenes*), *Treponoma* (e.g., *Treponoma pallidum*), *Vibrio* (e.g., *Vibrio cholerae, Vibrio vulnificus*), and *Yersinia* (e.g., *Yersinia pestis*). Libraries for other bacteria can also be produced and used according to methods described herein.

In some embodiments, members of a library include polynucleotides that encode polypeptides from protozoa. Examples of protozoal pathogens include the following organisms: *Cryptosporidium parvum, Entamoeba* (e.g., *Entamoeba histolytica*), *Giardia* (e.g., *Giardia lambila*), *Leishmania* (e.g., *Leishmania donovani*), *Plasmodium* spp. (e.g., *Plasmodium falciparum, Plasmodium vivax, Plasmodium ovale, Plasmodium malariae*), *Toxoplasma* (e.g., *Toxoplasma gondii*), *Trichomonas* (e.g., *Trichomonas vaginalis*), and *Trypanosoma* (e.g., *Trypanosoma brucei, Trypanosoma cruzi*). Libraries for other protozoa can also be produced and used according to methods described herein.

In some embodiments, members of a library include polynucleotides that encode polypeptides from a fungus. Examples of fungal pathogens include the following: *Aspergillus, Candida* (e.g., *Candida albicans*), *Coccidiodes* (e.g., *Coccidiodes immitis*), *Cryptococcus* (e.g., *Cryptococcus neoformans*), *Histoplasma* (e.g., *Histoplasma capsulatum*), and *Pneumocystis* (e.g., *Pneumocystis carinii*). Libraries for other fungi can also be produced and used according to methods described herein.

In some embodiments, members of a library include polynucleotides that encode polypeptides from a helminth Examples of helminthic pathogens include *Ascaris lumbricoides, Ancylostoma, Clonorchis sinensis, Dracuncula medinensis, Enterobius vermicularis, Filaria, Onchocerca volvulus, Loa loa, Schistosoma, Strongyloides, Trichuris trichura,* and *Trichinella spiralis*. Libraries for other helminths can also be produced and used according to methods described herein.

Sequence information for genomes and ORFs for infectious agents is publicly available. See, e.g., the Entrez Genome Database (URL: ncbi.nlm.nih.gov/sites/entrez?db=Genome&itool=toolbar) and the ERGO™ Database (URL: igweb.integratedgenomics.com/ERGO_supplement/genomes.html), the Genomes Online Database (GOLD) (URL: genomesonline.org) (Liolios et al., *Nucleic Acids Res.* 1; 34 (Database issue):D332-4, 2006).

In some embodiments, a library includes polynucleotides that express human polypeptides. Such libraries are useful, e.g., for identifying candidate tumor antigens, or targets of autoreactive immune responses. An exemplary library for identifying tumor antigens includes polynucleotides encoding polypeptides that are differentially expressed or otherwise altered in tumor cells. An exemplary library for evaluating autoreactive immune responses includes polynucleotides expressed in the tissue against which the autoreactive response is directed (e.g., a library containing pancreatic polynucleotide sequences is used for evaluating an autoreactive immune response against the pancreas).

As noted above, library members can express a cytolysin polypeptide, in addition to a heterologous polypeptide. In some embodiments, the cytolysin polypeptide is heterologous to the library cell in which it is expressed, and facilitates delivery of polypeptides expressed by the library cell into the cytosol of a human cell that has internalized the library cell. Cytolysin polypeptides include bacterial cytolysin polypeptides, such as listeriolysin O (LLO), streptolysin O (SLO), and perfringolysin O (PFO). Additional cytolysin polypeptides are described in U.S. Pat. No. 6,004,815. In certain embodiments, library members express LLO. In some embodiments, a cytolysin polypeptide is not significantly secreted by the library cell (e.g., less than 20%, 10%, 5%, or 1% of the cytolysin polypeptide produced by the cell is secreted). For example, the cytolysin polypeptide is a cytoplasmic cytolysin polypeptide, such as a cytoplasmic LLO polypeptide (e.g., a form of LLO which lacks the N-terminal signal sequence, as described in Higgins et al., *Mol. Microbiol.* 31(6):1631-1641, 1999). Exemplary cytolysin polypeptide sequences are shown in Table 1. The listeriolysin O (Δ3-25) sequence shown in the second row of Table 1 has a deletion of residues 3-25, relative to the LLO sequence in shown in the first row of Table 1, and is a cytoplasmic LLO polypeptide. In some embodiments, a cytolysin is expressed constituitively in a library host cell. In other embodiments, a cytolysin is expressed under the control of an inducible promoter. Cytolysin polypeptides can be expressed from the same vector, or from a different vector, as the heterologous polypeptide in a library cell.

TABLE 1

Exemplary Cytolysin Polypeptides

| Polypeptide Name (species) | Polypeptide Accession No. GI No. | Polypeptide Sequence |
|---|---|---|
| listeriolysin O (*Listeria monocytogenes*) | NP_463733.1 GI: 16802248 | MKKIMLVFITLILVSLPIAQQTEAKDASAFNKENSISSMA PPASPPASPKTPIEKKHADEIDKYIQGLDYNKNNVLVYHG DAVTNVPPRKGYKDGNEYIVVEKKKKSINQNNADIQVVNA ISSLTYPGALVKANSELVENQPDVLPVKRDSLTLSIDLPG MTNQDNKIVVKNATKSNVNNAVNTLVERWNEKYAQAYPNV SAKIDYDDEMAYSESQLIAKFGTAFKAVNNSLNVNFGAIS EGKMQEEVISFKQIYYNVNVNEPTRPSRFFGKAVTKEQLQ ALGVNAENPPAYISSVAYGRQVYLKLSTNSHSTKVKAAFD AAVSGKSVSGDVELTNIIKNSSFKAVIYGGSAKDEVQIID GNLGDLRDILKKGATFNRETPGVPIAYTTNFLKDNELAVI KNNSEYIETTSKAYTDGKINIDHSGGYVAQFNISWDEVNY DPEGNEIVQHKNWSENNKSKLAHFTSSIYLPGNARNINVY AKECTGLAWEWWRTVIDDRNLPLVKNRNISIWGTTLYPKY SNKVDNPIE (SEQ ID NO: 1) |
| listeriolysin O (Δ3-25) | | MKDASAFNKENSISSMAPPASPPASPKTPIEKKHADEIDK YIQGLDYNKNNVLVYHGDAVTNVPPRKGYKDGNEYIVVEK KKKSINQNNADIQVVNAISSLTYPGALVKANSELVENQPD VLPVKRDSLTLSIDLPGMTNQDNKIVVKNATKSNVNNAVN TLVERWNEKYAQAYPNVSAKIDYDDEMAYSESQLIAKFGT AFKAVNNSLNVNFGAISEGKMQEEVISFKQIYYNVNVNEP TRPSRFFGKAVTKEQLQALGVNAENPPAYISSVAYGRQVY LKLSTNSHSTKVKAAFDAAVSGKSVSGDVELTNIIKNSSF KAVIYGGSAKDEVQIIDGNLGDLRDILKKGATFNRETPGV PIAYTTNFLKDNELAVIKNNSEYIETTSKAYTDGKINIDH SGGYVAQFNISWDEVNYDPEGNEIVQHKNWSENNKSKLAH FTSSIYLPGNARNINVYAKECTGLAWEWWRTVIDDRNLPL VKNRNISIWGTTLYPKYSNKVDNPIE (SEQ ID NO: 2) |
| streptolysin O (*Streptococcus pyogenes*) | BAB41212.2 GI: 71061060 | MSNKKTFKKYSRVAGLLTAALIIGNLVTANAESNKQNTAS TETTTTSEQPKPESSELTIEKAGQKMDDMLNSNDMIKLAP KEMPLESAEKEEKKSEDKKKSEEDHTEEINDKIYSLNYNE LEVLAKNGETIENFVPKEGVKKADKFIVIERKKKNINTTP VDISIIDSVTDRTYPAALQLANKGFTENKPDAVVTKRNPQ KIHIDLPGMGDKATVEVNDPTYANVSTAIDNLVNQWHDNY SGGNTLPARTQYTESMVYSKSQIEAALNVNSKILDGTLGI DFKSISKGEKKVMIAAYKQIFYTVSANLPNNPADVFDKSV TFKDLQRKGVSNEAPPLFVSNVAYGRTVFVKLETSSKSND VEAAFSAALKGTDVKTNGKYSDILENSSFTAVVLGGDAAE HNKVVTKDFDVIRNVIKDNATFSRKNPAYPISYTSVFLKN NKIAGVNNRTEYVETTSTEYTSGKINLSHQGAYVAQYEIL WDEINYDDKGKEVITKRRWDNNWYSKTSPFSTVIPLGANS RNIRIMARECTGLAWEWWRKVIDERDVKLSKEINVNISGS TLSPYGSITYK (SEQ ID NO: 3) |
| perfringolysin O (*Clostridium perfringens*) | NP_561079.1 GI: 18309145 | MIRFKKTKLIASIAMALCLFSQPVISFSKDITDKNQSIDS GISSLSYNRNEVLASNGDKIESFVPKEGKKTGNKFIVVER QKRSLTTSPVDISIIDSVNDRTYPGALQLADKAFVENRPT ILMVKRKPININIDLPGLKGENSIKVDDPTYGKVSGAIDE LVSKWNEKYSSTHTLPARTQYSESMVYSKSQISSALNVNA KVLENSLGVDFNAVANNEKKVMILAYKQIFYTVSADLPKN PSDLFDDSVTFNDLKQKGVSNEAPPLMVSNVAYGRTIYVK LETTSSSKDVQAAFKALIKNTDIKNSQQYKDIYENSSFTA VVLGGDAQEHNKVVTKDFDEIRKVIKDNATFSTKNPAYPI SYTSVFLKDNSVAAVHNKTDYIETTSTEYSKGKINLDHSG AYVAQFEVAWDEVSYDKEGNEVLTHKTWDGNYQDKTAHYS TVIPLEANARNIRIKARECTGLAWEWWRDVISEYDVPLTN NINVSIWGTTLYPGSSITYN (SEQ ID NO: 4) |

In some embodiments, a library member (e.g., a library member which is a bacterial cell) includes an invasin that facilitates uptake by the antigen presenting cell. In some embodiments, a library member includes an autolysin that facilitates autolysis of the library member within the antigen presenting cell. In some embodiments, a library member includes both an invasin and an autolysin. In some embodiments, a library member which is an *E. coli* cell includes an invasin and/or an autolysin. In various embodiments, library cells that express an invasin and/or autolysin are used in methods that also employ non-professional antigen presenting cells or antigen presenting cells that are from cell lines. Isberg et al. (*Cell*, 1987, 50:769-778), Sizemore et al. (*Science*, 1995, 270:299-302) and Courvalin et al. (*C. R. Acad. Sci. Paris*, 1995, 318:1207-12) describe expression of an invasin to effect endocytosis of bacteria by target cells. Autolysins are described by Cao et al., *Infect. Immun.* 1998, 66(6): 2984-2986; Margot et al., *J. Bacteriol.* 1998, 180(3):749-752; Buist et al., *Appi. Environ. Microbiol.*, 1997, 63(7):2722-2728; Yamanaka et al., *FEMS Microbiol. Lett.*, 1997, 150(2): 269-275; Romero et al., *FEMS Microbiol. Lett.*, 1993, 108 (1):87-92; Betzner and Keck, *Mol. Gen. Genet.*, 1989, 219(3): 489-491; Lubitz et al., *J. Bacteriol.*, 1984, 159(1):385-387; and Tomasz et al., *J. Bacteriol.*, 1988, 170(12): 5931-5934. In some embodiments, an autolysin has a feature that permits delayed lysis, e.g., the autolysin is temperature-sensitive or time-sensitive (see, e.g., Chang et al., 1995, *J. Bact.* 177, 3283-3294; Raab et al., 1985, *J. Mol. Biol.* 19, 95-105; Gerds et al., 1995, *Mol. Microbiol.* 17, 205-210). Useful cytolysins also include addiction (poison/antidote) autolysins, (see, e.g., Magnuson R, et al., 1996, *J. Biol. Chem.* 271(31), 18705-18710; Smith A S, et al., 1997, *Mol. Microbiol.* 26(5), 961-970).

In most embodiments, a member of a library expresses a single heterologous polypeptide of an infectious agent or target cell. In some embodiments, a cell of a library expresses multiple heterologous polypeptides. Sets of library members (e.g., bacterial cells) can be provided on an array (e.g., on a solid support, such as a 96-well plate) and separated such that members in each location express a different heterologous polypeptide, or a different set of heterologous polypeptides.

Methods of using library members for identifying T cell antigens are described in detail below. In addition to these methods, library members also have utility in assays to identify B cell antigens. For example, lysate prepared from library members that include heterologous polypeptides can be used to screen a sample comprising antibodies (e.g., a serum sample) from an individual (e.g., an individual that has been exposed to an infectious agent of interest), to determine whether antibodies present in the individual react with the heterologous polypeptide. Suitable methods for evaluating antibody reactivity are known and include ELISA assays.

Library Screens

Human Cells for Antigen Presentation

The present invention provides, inter alia, compositions and methods for identifying antigens recognized by human immune cells. Human antigen presenting cells express ligands for antigen receptors and other immune activation molecules on human lymphocytes. Given differences in MHC peptide binding specificities and antigen processing enzymes between species, antigens processed and presented by human cells are more likely to be physiologically relevant human antigens in vivo than antigens identified in non-human systems. Accordingly, methods of identifying these antigens employ human cells to present candidate antigen polypeptides.

Any human cell that internalizes library members and presents polypeptides expressed by the library members on MHC molecules can be used as an antigen presenting cell according to the present invention. In some embodiments, human cells used for antigen presentation are primary human cells. The cells can include peripheral blood mononuclear cells (PBMC) of a human. In some embodiments, peripheral blood cells are separated into subsets (e.g., subsets comprising dendritic cells, macrophages, monocytes, B cells, or combinations thereof) prior to use in an antigen presentation assay. In some embodiments, a subset of cells that expresses MHC class II is selected from peripheral blood. In one example, a cell population including dendritic cells is isolated from peripheral blood. In some embodiments, a subset of dendritic cells is isolated (e.g., plasmacytoid, myeloid, or a subset thereof). Human dendritic cell markers include CD1c, CD1a, CD303, CD304, CD141, and CD209. Cells can be selected based on expression of one or more of these markers (e.g., cells that express CD303, CD1c, and CD141).

Dendritic cells can be isolated by positive selection from peripheral blood using commercially available kits (e.g., from Miltenyi Biotec Inc.). Dendritic cells can also be produced by culturing peripheral blood cells under conditions that promote differentiation of monocyte precursors into dendritic cells in vitro. These conditions typically include culturing the cells in the presence of cytokines such as GM-CSF and IL-4 (see, e.g., Inaba et al., Isolation of dendritic cells, *Curr. Protoc. Immunol.* May; Chapter 3: Unit 3.7, 2001). Procedures for in vitro expansion of hematopoietic stem and progenitor cells (e.g., taken from bone marrow or peripheral blood), and differentiation of these cells into dendritic cells in vitro, is described in U.S. Pat. No. 5,199,942, and U.S. Pat. Pub. 20030077263. Briefly, CD34[+] hematopoietic stem and progenitor cells are isolated from peripheral blood or bone marrow and expanded in vitro in culture conditions that include one or more of Flt3-L, IL-1, IL-3, and c-kit ligand.

In some embodiments, immortalized cells that express human MHC molecules (e.g., human cells, or non-human cells that are engineered to express human MHC molecules) are used for antigen presentation. For example, assays can employ COS cells transfected with human MHC molecules or HeLa cells.

In some embodiments, primary human cells are used in a method described herein and both the antigen presenting cells and immune cells used in the method are derived from the same subject (e.g., autologous T cells and APC are used). In these embodiments, it can be advantageous to sequentially isolate subsets of cells from peripheral blood of the subject, to maximize the yield of cells available for assays. For example, one can first isolate CD4[+] and CD8[+] T cell subsets from the peripheral blood. Next, dendritic cells (DC) are isolated from the T cell-depleted cell population. The remaining T- and DC-depleted cells are used to supplement the DC in assays, or are used alone as antigen presenting cells. In some embodiments, DC are used with T- and DC-depleted cells in an assay, at a ratio of 1:2, 1:3, 1:4, or 1:5.

Antigen presenting cells can be isolated from sources other than peripheral blood. For example, antigen presenting cells can be taken from a mucosal tissue (e.g., nose, mouth, bronchial tissue, tracheal tissue, the gastrointestinal tract, the genital tract (e.g., vaginal tissue), or associated lymphoid tissue), peritoneal cavity, lymph nodes, spleen, bone marrow, thymus, lung, liver, kidney, neuronal tissue, endocrine tissue, or other tissue, for use in screening assays. In some embodiments, cells are taken from a tissue that is the site of an active immune response (e.g., an ulcer, sore, or abscess). Cells may be isolated from tissue removed surgically, via lavage, or other means.

Antigen presenting cells useful in methods described herein are not limited to "professional" antigen presenting cells. Surprisingly, the present inventors have demonstrated that non-professional antigen presenting cells can be utilized effectively in the practice of the present invention. Non-professional antigen presenting cells include fibroblasts, epithelial cells, endothelial cells, neuronal/glial cells, lymphoid or myeloid cells that are not professional antigen presenting cells (e.g., T cells, neutrophils), muscle cells, liver cells, and other types of cells.

Antigen presenting cells are cultured with library members that express a heterologous polypeptide (and, if desired, a cytolysin polypeptide) under conditions in which the antigen presenting cells internalize, process and present polypeptides expressed by the library members on MHC molecules. In some embodiments, library members are killed or inactivated prior to culture with the antigen presenting cells. Cells or viruses can be inactivated by any appropriate agent (e.g., fixation with organic solvents, irradiation, freezing). In some embodiments, the library members are cells that express ORFs linked to a tag (e.g., a tag which comprises one or more known T cell epitopes), expression of which has been verified prior to the culturing.

In some embodiments, antigen presenting cells are incubated with library members at 37° C. for between 30 minutes and 5 hours (e.g., for 45 min. to 1.5 hours). After the incubation, the antigen presenting cells can be washed to remove library members that have not been internalized. In certain embodiments, the antigen presenting cells are non-adherent, and washing requires centrifugation of the cells. The washed antigen presenting cells can be incubated at 37° C. for an additional period of time (e.g., 30 min. to 2 hours) prior to exposure to lymphocytes, to allow antigen processing. In some embodiments, it is desirable to fix and kill the antigen presenting cells prior to exposure to lymphocytes (e.g., by treating the cells with 1% paraformaldehyde).

The antigen presenting cell and library member numbers can be varied, so long as the library members provide quantities of heterologous polypeptides sufficient for presentation on MHC molecules. In some embodiments, antigen presenting cells are provided in an array, and are contacted with sets of library cells, each set expressing a different heterologous polypeptide. In certain embodiments, each location in the array includes $1 \times 10^3$-$1 \times 10^6$ antigen presenting cells, and the cells are contacted with $1 \times 10^3$-$1 \times 10^8$ library cells which are bacterial cells.

In any of the embodiments described herein, antigen presenting cells can be freshly isolated, maintained in culture, or thawed from frozen storage prior to incubation with library cells, or after incubation with library cells.

Human Lymphocytes

In methods of the present invention, human lymphocytes are tested for antigen specific reactivity to antigen presenting cells, e.g., antigen presenting cells that have been incubated with libraries expressing candidate antigen polypeptides as described above. The methods of the present invention permits rapid identification of human antigens using pools of lymphocytes isolated from an individual, or progeny of the cells. The detection of antigen specific responses does not rely on laborious procedures to isolate individual T cell clones. In some embodiments, the human lymphocytes are primary lymphocytes. Just as antigen presenting cells may be separated into subsets prior to use in antigen presentation assays, a population of lymphocytes having a specific marker or other feature can be used. In some embodiments, a population of T lymphocytes is isolated. In some embodiments, a population of $CD4^+$ T cells is isolated. In some embodiments, a population of $CD8^+$ T cells is isolated. $CD8^+$ T cells recognize peptide antigens presented in the context of MHC class 1 molecules. Thus, in some embodiments, the $CD8^+$ T cells are used with antigen presenting cells that have been exposed to library host cells that co-express a cytolysin polypeptide, in addition to a candidate antigen. T cell subsets that express other cell surface markers may also be isolated, e.g., to provide cells having a particular phenotype. These include CLA (for skin-homing T cells), CD25, CD30, CD69, CD154 (for activated T cells), CD45RO (for memory T cells), CD294 (for Th2 cells), $\gamma/\delta$ TCR-expressing cells, CD3 and CD56 (for NK T cells). Other subsets can also be selected.

Lymphocytes can be isolated, and separated, by any means known in the art (e.g., using antibody-based methods such as those that employ magnetic bead separation, panning, or flow cytometry). Reagents to identify and isolate human lymphocytes and subsets thereof are well known and commercially available.

Lymphocytes for use in methods described herein can be isolated from peripheral blood mononuclear cells, or from other tissues in a human. In some embodiments, lymphocytes are taken from lymph nodes, a mucosal tissue (e.g., nose, mouth, bronchial tissue, tracheal tissue, the gastrointestinal tract, the genital tract (e.g., vaginal tissue), or associated lymphoid tissue), peritoneal cavity, spleen, thymus, lung, liver, kidney, neuronal tissue, endocrine tissue, peritoneal cavity, bone marrow, or other tissues. In some embodiments, cells are taken from a tissue that is the site of an active immune response (e.g., an ulcer, sore, or abscess). Cells may be isolated from tissue removed surgically, via lavage, or other means.

Lymphocytes taken from an individual can be maintained in culture or frozen until use in antigen presentation assays. Surprisingly, the inventors have found that freshly isolated lymphocytes can be stimulated in vitro by antigen presenting cells exposed to library cells as described above. These lymphocytes exhibit detectable stimulation without the need for prior non-antigen specific expansion. However, primary lymphocytes also elicit detectable antigen specific responses when first stimulated nonspecifically in vitro. Thus, in some embodiments, lymphocytes are stimulated to proliferate in vitro in a non antigen-specific manner, prior to use in an antigen presentation assay. Lymphocytes can also be stimulated in an antigen-specific manner prior to use in an antigen presentation assay. For example, cells from an individual thought to have been exposed to a virus can be stimulated with antigen presenting cells infected with the virus, or pulsed with a composition comprising viral antigens (e.g., viral lysate, or recombinant polypeptides). In some embodiments, cells are stimulated to proliferate by a library (e.g., prior to use in an antigen presentation assay that employs the library). Expanding cells in vitro provides greater numbers of cells for use in assays. Primary T cells can be stimulated to expand, e.g., by exposure to a polyclonal T cell mitogen, such as phytohemagglutinin or concanavalin, by treatment with antibodies that stimulate proliferation, or by treatment with particles coated with the antibodies. In some embodiments, T cells are expanded by treatment with anti-CD2, anti-CD3, and anti-CD28 antibodies.

Antigen Presentation Assays

In antigen presentation assays, T cells are cultured with antigen presenting cells prepared according to the methods described above, under conditions that permit T cell recognition of peptides presented by MHC molecules on the antigen presenting cells. In some embodiments, T cells are incubated with antigen presenting cells at 37° C. for between 12-48 hours (e.g., for 24 hours). In some embodiments, T cells are incubated with antigen presenting cells at 37° C. for 3, 4, 5, 6, 7, or 8 days. Numbers of antigen presenting cells and T cells can be varied. In some embodiments, the ratio of T cells to antigen presenting cells in a given assay is 1:10, 1:5, 1:2, 1:1, 2:1, 5:1, or 10:1. In some embodiments, antigen presenting cells are provided in an array (e.g., in a 96-well plate), wherein cells in each location of the array have been contacted with sets of library cells, each set including a different heterologous polypeptide. In certain embodiments, each location in the array includes $1 \times 10^3$-$1 \times 10^6$ antigen presenting cells, and the cells are contacted with $1 \times 10^3$-$1 \times 10^6$ T cells.

After T cells have been incubated with antigen presenting cells, cultures are assayed for stimulation. Lymphocyte stimulation can be detected by any means known in the art. In some embodiments, culture supernatants are harvested and assayed for secretion of a polypeptide associated with activation, e.g., a cytokine, such as IFNγ, TNFα, TNFβ interleukin-2 (IL-2), IL-4, IL-5, IL-3, IL-10, IL-17, TGFβ, or GM-CSF. Cytokine secretion in culture supernatants can be detected, e.g., by ELISA, bead array, e.g., with a Luminex® analyzer. Cytokine production can also be assayed by RT-PCR of mRNA isolated from the T cells, or by ELISPOT analysis of cytokines released by the T cells. Other polypeptides associated with T cell activation, which may be assayed to detect stimulation, include perforin, granzyme, Fas ligand and CD40 ligand, CD25, and CD69. In some embodiments, proliferation of T cells in the cultures is determined (e.g., by detecting $^3$H thymidine incorporation). In some embodiments, target cell lysis is determined (e.g., by detecting T cell dependent lysis of antigen presenting cells labeled with $Na_2^{51}CrO_4$). Target cell lysis assays are typically performed with CD8$^+$ T cells. Protocols for these detection methods are known. See, e.g., *Current Protocols In Immunology*, John E. Coligan et al. (eds), Wiley and Sons, New York, N.Y., 2007. One of skill in the art understands that appropriate controls are used in these detection methods, e.g., to adjust for non-antigen-specific background activation, to confirm the stimulatory capacity of antigen presenting cells, and to confirm the viability of lymphocytes.

In some embodiments, antigen presentation assays are repeated using antigen presenting cell and lymphocytes from different individuals, e.g., to identify antigens recognized by multiple individuals, or compare reactivities that differ between individuals.

Applications

After it is determined that a heterologous polypeptide presented by an antigen presenting cell in an assay described herein stimulates human lymphocytes, the heterologous polypeptide, now identified as an antigen, can be produced and incorporated into compositions for use in eliciting immune responses. These and other applications are discussed below.

Human Cell Donors

One advantage of methods described herein is their ability to identify clinically relevant human antigens. Humans that have been exposed to an immunogenic stimulus (e.g., from natural infection by an infectious agent) contain lymphocytes that specifically recognize antigens of the infectious agent, which are the product of an adaptive immune response arising from the prior exposure. In some embodiments, these cells are present at a higher frequency than cells from a naive individual, and/or the cells are readily reactivated when reexposed to the proper antigenic stimulus (e.g., the cells are "memory" cells). Thus, humans that have been exposed to an infectious agent are particularly useful donors of cells for identifying antigens in vitro. The individual may be one who has recovered from the infection, or one who has been exposed to the infectious agent and remained asymptomatic. In some embodiments, the individual has been recently infected with the infectious agent (e.g., the individual was infected with the infectious agent less than three months, two months, one month, or two weeks, prior to isolation of lymphocytes and/or antigen presenting cells from the individual). In some embodiments, the individual was first infected with the agent more than three months, six months, or one year prior to isolation of lymphocytes and/or antigen presenting cells. In some embodiments, the individual is latently or persistently infected with the infectious agent. In some embodiments, the individual has been vaccinated against an infectious agent of interest (e.g., with a whole cell bacterial vaccine, attenuated viral, peptide, or nucleic acid vaccine). Methods herein may be used to analyze an immune response to a vaccine vector itself. For example, cells of a patient immunized with a bacterial or viral vector that carries on or more antigens of a heterologous organism can be isolated and analyzed to characterize an immune response against the bacterial or viral vector. In some embodiments, the cells from the individual are screened in assays in which antigen presenting cells have been contacted with a library of cells whose members express polypeptides from the infectious agent, or a related species thereof.

In certain embodiments, cells from an individual who has been exposed to an infectious agent are used to identify antigens in a related species. In some embodiments, the infectious agent is a virus, and the related species is a virus in the same family. To give one example, cells from a patient infected with Epstein-Barr Virus (EBV) can be screened against antigen presenting cells that have been incubated with a library expressing polypeptides from Herpes Simplex Virus-2 (HSV-2). Polypeptides identified in such a screen may be useful as antigens that elicit broadly cross-reactive immune responses protective against multiple types of herpes viruses.

In some embodiments, lymphocytes are screened against antigen presenting cells that have been contacted with a library of cells whose members express polypeptides from an infectious agent, and the lymphocytes are from an individual who has not been exposed to the infectious agent. In some embodiments, such lymphocytes are used to determine background (i.e., non-antigen-specific) reactivities. In some embodiments, such lymphocytes are used to identify antigens, reactivity to which exists in naïve individuals.

Cells from multiple donors can be collected and assayed in methods described herein. In some embodiments, cells from multiple donors are assayed in order to verify that a given antigen is reactive in a broad portion of the population, or to identify multiple antigens that can be later combined to produce an immunogenic composition that will be effective in a broad portion of the population.

The methods described herein have applications that extend beyond antigen identification. For example, the ability to rapidly detect human antigen specific T cell responses in vitro can be used to determine whether an individual has been exposed to an infectious agent or set of infectious agents. In some embodiments, antigen presentation assays are used to evaluate qualitative aspects of an individual's prior, or ongoing, immunological reaction to an infectious agent. Some infectious agents such as mycobacteria and hepatitis viruses cause persistent infections. Other infectious agents are not eliminated effectively by the immune response in patients. Comparing the types of antigenic reactivities associated with persistent infections and successful immunity to these agents can aid in the design of immunogenic compositions that will be likely to provide protection. By way of example, in some embodiments, methods described herein are used to compare antigenic reactivities found in patients suffering from disseminated herpes infections to those of patients in which a herpes infection was resolved. These analyses may reveal antigenic reactivities prominent in resolved infections and lacking in disseminated infections. To provide another example, in some embodiments, methods herein are used to compare antigenic reactivities in patients suffering from pelvic inflammatory disease (PID) due to an infectious agent such as *C. trachomatis* or *N. gonorrhoeae* to patients exposed to those agents, and that do not present with pelvic inflammatory disease. The identification of antigens associated with a particular pathological form of infection facilitates development of diagnostic assays to monitor the course of infection and determine the likelihood of developing the pathology. For example, antigens identified as associated with PID can be used in diagnostic assays for patients that are infected with a causative agent, and that have not yet developed PID, to help evaluate the likelihood of occurrence of this complication.

In still other, related embodiments, antigen presentation assays as described herein are used to evaluate an individual's response to an infectious agent to determine the stage of infection. For example, the presence of reactivity to an antigen only expressed in a latent or persistent phase of an infection can indicate that the infection has progressed to one of these stages. In some embodiments, antigen presentation assays as described herein are used to evaluate responses of subjects undergoing therapeutic treatment for an infection. In some embodiments, antigen presentation assays as described herein are used to evaluate responses of subjects who have been administered an immunogenic composition (e.g., as part of a clinical trial for a candidate vaccine).

Antigen presentation assays are useful in the context of non-infectious diseases as well. The methods described herein are applicable to any context in which a rapid evaluation of human cellular immunity is beneficial. In some embodiments, antigenic reactivity to polypeptides that are differentially expressed by neoplastic cells (e.g., tumor cells) is evaluated. Sets of nucleic acids differentially expressed by neoplastic cells have been identified using established techniques such as subtractive hybridization. Methods described herein can be used to identify antigens that were functional in a subject in which an anti-tumor immune response occurred. In other embodiments, methods are used to evaluate whether a subject has lymphocytes that react to a tumor antigen or set of tumor antigens. In some embodiments, antigen presentation assays are used to examine reactivity to autoantigens in cells of an individual, e.g., an individual predisposed to, or suffering from, an autoimmune condition. Such methods can be used to provide diagnostic or prognostic indicators of the individual's disease state, or to identify autoantigens. For these assays, in some embodiments, libraries that include an array of human polypeptides are prepared. In some embodiments, libraries that include polypeptides from infectious agents which are suspected of eliciting cross-reactive responses to autoantigens are prepared. For examples of antigens from infectious agents thought to elicit cross-reactive autoimmune responses, see Barzilai et al., *Curr Opin Rheumatol.*, 19(6):636-43, 2007; Ayada et al., *Ann N Y Acad Sci.*, 1108:594-602, 2007; Drouin et al., *Mol Immunol.*, 45(1):180-9, 2008; and Bach, *J Autoimmun.*, 25 Suppl:74-80, 2005.

Epitope Identification

The present invention includes methods in which heterologous polypeptides are expressed in library cells. After library cells are internalized by antigen presenting cells, the heterologous polypeptides are proteolytically processed within the antigen presenting cells, and peptide fragments of the heterologous polypeptides are presented on MHC molecules expressed in the antigen presenting cells. The identity of the heterologous polypeptide that stimulates a human lymphocyte in an assay described herein can be determined from examination of the set of library cells that were provided to the antigen presenting cells that produced the stimulation. In some embodiments, it is useful to map the epitope within the heterologous polypeptide which is bound by MHC molecules to produce the observed stimulation. This epitope, or the longer polypeptide from which it is derived (both of which are referred to as an "antigen" herein) can form the basis for an immunogenic composition, or for an antigenic stimulus in future antigen presentation assays.

Methods for identifying peptides bound by MHC molecules are known. In some embodiments, epitopes are identified by generating deletion mutants of the heterologous polypeptide and testing these for the ability to stimulate lymphocytes. Deletions which lose the ability to stimulate lymphocytes, when processed and presented by antigen presenting cells, have lost the peptide epitope. In some embodiments, epitopes are identified by synthesizing peptides corresponding to portions of the heterologous polypeptide and testing the peptides for the ability to stimulate lymphocytes (e.g., in antigen presentation assays in which antigen presenting cells are pulsed with the peptides). Other methods for identifying MHC bound peptides involve lysis of the antigen presenting cells that include the antigenic peptide, affinity purification of the MHC molecules from cell lysates, and subsequent elution and analysis of peptides from the MHC (Falk, K. et al. *Nature* 351:290, 1991, and U.S. Pat. No. 5,989,565).

Immunogenic Compositions and Uses Thereof

The invention provides compositions that include an antigen or antigens identified by methods described herein nucleic acids encoding the antigens, and methods of using the compositions. In some embodiments, a composition includes antigens which are peptides 8-40 amino acids in length (e.g., MHC binding peptides, e.g., peptides 8-25, 8-20, 8-15, 8-12 amino acids in length). In some embodiments, a composition includes antigens which are polypeptides (e.g., polypeptides encoded by full length open reading frames of an infectious agent, or portions thereof). The compositions can include antigens which are, or which comprise, MHC class I-binding peptides, MHC class II-binding peptides, or both MHC class I and MHC class II-binding peptides. Compositions can include a single antigen, or multiple antigens. In some embodiments, a composition includes a set of two, three, four, five, six, seven, eight, nine, ten, or more antigens. In some embodiments, the set of antigens is from a single infectious agent. In some embodiments, the set of antigens is from two infectious agents.

The invention also provides nucleic acids encoding the antigens. The nucleic acids can be used to produce expression vectors, e.g., for recombinant production of the antigens, or for nucleic acid-based administration in vivo (e.g., DNA vaccination).

In some embodiments, antigens are used in diagnostic assays. For these assays, compositions including the antigens can be provided in kits, e.g., for detecting antibody reactivity, or cellular reactivity, in a sample from an individual.

In some embodiments, antigen compositions are used to induce an immune response in a subject. In some embodiments, the subject is a human. In some embodiments, the subject is a non-human animal. The antigen compositions can be used to raise antibodies (e.g., in a non-human animal, such as a mouse, rat, hamster, or goat), e.g., for use in diagnostic assays, and for therapeutic applications. For an example of a therapeutic use, an antigen discovered by a method described herein may be a potent T cell and B cell antigen, antibodies to which provide protective immunity in vivo by neutralizing an infectious agent. Preparations of neutralizing antibodies may be produced by immunizing a subject with the antigen and isolating antiserum from the subject. Methods for eliciting high titers of high affinity, antigen specific antibodies, and for isolating the antigen specific antibodies from antisera, are known in the art. In some embodiments, the antigen compositions are used to raise monoclonal antibodies, e.g., human monoclonal antibodies.

In some embodiments, an antigen composition is used to induce an immune response in a human subject to provide protection from infection, or to provide a therapeutic response. The protection can be complete or partial protection. In some embodiments, an antigen composition elicits an immune response to an infectious agent that causes the subject to have milder symptoms and/or a shorter duration of illness, when exposed to the infectious agent, e.g., as compared to a subject that has not been administered the antigen composition. In some embodiments, where a therapeutic response is desired, the antigen composition elicits a response that reduces symptoms or duration of illness associated with the infection, or reduced levels of the infectious agent, in the subject, e.g., as compared to a subject that has not been administered the antigen composition.

In some embodiments, immunogenicity of an antigen is evaluated in vivo. In some embodiments, humoral responses to an antigen are evaluated (e.g., by detecting antibody titers to the administered antigen). In some embodiments, cellular immune responses to an antigen are evaluated, e.g., by detecting the frequency of antigen-specific cells in a sample from the subject (e.g., by staining T cells from the subject with MHC/peptide tetramers containing the antigenic peptide, to detect antigen specific T cells, or by detecting antigen specific cells using an antigen presentation assay such as an assay described herein). In some embodiments, the ability of an antigen or antigens to elicit protective or therapeutic immunity is evaluated in an animal model.

In some embodiments, the composition includes a pharmaceutically acceptable carrier or excipient. An immunogenic composition may also include an adjuvant for enhancing the immunogenicity of the formulation, (e.g., oil in water, incomplete Freund's adjuvant, aluminum phosphate, aluminum hydroxide, saponin adjuvants, or muramyl dipeptides). Other adjuvants are known in the art.

In some embodiments, an immunogenic composition includes an antigen linked to a carrier protein. Examples of carrier proteins include, e.g., toxins and toxoids (chemical or genetic), which may or may not be mutant, such as anthrax toxin, PA and DNI (PharmAthene, Inc.), diphtheria toxoid (Massachusetts State Biological Labs; Serum Institute of India, Ltd.) or CRM 197, tetanus toxin, tetanus toxoid (Massachusetts State Biological Labs; Serum Institute of India, Ltd.), tetanus toxin fragment Z, exotoxin A or mutants of exotoxin A of *Pseudomonas aeruginosa*, bacterial flagellin, pneumolysin, an outer membrane protein of *Neisseria meningitidis* (strain available from the ATCC (American Type Culture Collection, Manassas, Va.)), *Pseudomonas aeruginosa* Hcp1 protein, *E. coli* heat labile enterotoxin, shiga-like toxin, human LTB protein, a protein extract from whole bacterial cells, and any other protein that can be cross-linked by a linker. Other useful carrier proteins include bovine serum albumin (BSA), P40, and chicken riboflavin. Many carrier proteins are commercially available (e.g., from Sigma Aldrich.).

In some embodiments, an immunogenic composition including an antigen identified by a method described herein is used in conjunction with an available vaccine. For example, an antigen identified as described herein can be used as a supplemental component of a vaccine formulation, or as a boosting antigen in a vaccination protocol.

In some embodiments, an immunogenic composition is in a volume of about 0.5 mL for subcutaneous injection, 0.1 mL for intradermal injection, or 0.002-0.02 mL for percutaneous administration. A 0.5 ml dose of the composition may contain approximately 2-500 ug of the antigen.

In some embodiments an immunogenic composition is administered parenterally (for instance, by subcutaneous, intramuscular, intravenous, or intradermal injection). In some embodiments, delivery by a means that physically penetrates the dermal layer is used (e.g., a needle, airgun, or abrasion).

In some embodiments, an immunogenic composition is administered to a subject, e.g., by intramuscular injection, intradermal injection, or transcutaneous immunization with appropriate immune adjuvants. Compositions can be administered, one or more times, often including a second administration designed to boost an immune response in a subject. The frequency and quantity of dosage of the composition can vary depending on the specific activity of the composition and can be determined by routine experimentation.

The formulations of immunogenic compositions can be provided in unit-dose or multi-dose containers, for example, sealed ampoules and vials and may be stored in a freeze-dried (lyophilized) condition requiring only the addition of the sterile liquid carrier immediately prior to use.

EXEMPLIFICATION

Example 1

Preparation of a Library for Identification of Human Antigens from Herpes Simplex Virus-2

Library Generation

An expression library was created from herpes simplex virus-2 (HSV-2) via gene-specific PCR amplification of each coding region, followed by a second PCR reaction in which universal primers were used to append an additional recombination sequence (the Gateway™ system) onto the amplified sequences for cloning. In some cases, gene targets were synthesized by a commercial source and transferred within a plasmid vector.

PCR Primer Design

The open reading frames (ORFs) from the HSV-2 genome were generated using the published PubMed sequence under Accession No. NC_001798. Primers from all 77 genes were designed using the Primer3Plus software available at the following URL: bioinformatics.nl/cgi-bin/primer3plus/primer3plus.cgi. The coding sequences for each gene were imported into the Primer3Plus software and the software program calculated the primers based on set thresholds such as Tm. Proteins predicted to have a signal sequence were truncated so as to be expressed without the signal sequence. The forward primers were designed starting at the transcriptional start site, ATG, and the reverse primers were upstream of the stop codon. A universal sequence 5'-ACAAAAAAG-CAGGCTGC-3' (SEQ ID NO:5) was added to the 5' end of each forward primer and 5'-ACAAGAAAGCTGGGTAG-3'

(SEQ ID NO:6) was added to the 5' end of each reverse primer as an amplification site for addition of attP cloning sequences, as described in the Invitrogen Gateway Cloning manual.

PCR Amplification of Viral Genes

Each ORF was amplified in a 96-well plate with one ORF amplified per well, using the primer sets described above, Herculase enhanced DNA polymerase (Stratagene, LaJolla, Calif.) and purified genomic DNA (Advanced Biotechnologies Inc., Columbia, Md.). The PCR cycling parameters were 1 cycle at 98° C. for 4 minutes, followed by 30 cycles of 98° C. for 20 seconds, 60° C. for 20 seconds, 72° C. for 30 seconds, and 1 cycle of 72° C. for 3 minutes 30 seconds. Five microliters of the resulting products were reamplified with primers 5'-GGGACAAGTTTGTACAAAAAAGCAG-GCTGC-3' (SEQ ID NO:7) and 5'-GGGGACCACTTTGTA-CAAGAAAGCTGGGTAG-3' (SEQ ID NO:8) to add the attP cloning sequences to each product. The PCR cycling parameters were same as the first round of PCR. PCR products were run on 1.2% E-gel (Invitrogen, Carlsbad, Calif.) to verify the size of each the PCR products.

Cloning of PCR Products

The amplicons generated for each open reading frame were individually recombined into pDONR221 (Invitrogen) vector using BP Clonase II (Invitrogen) enzyme mix. Each reaction was incubated for 1 hour per kb of insert. All recombination reactions were transformed into Mach1 chemically competent cells (Invitrogen) with heat shock. The resulting transformant colonies were screened using colony PCR and consensus primers that amplified a small fragment of the vector in addition to the inserted clone. For the PCR, 25 µl reactions [2×PCR Master Mix (Promega, Madison, Wis.), 6% DMSO (Fisher, Pittsburg, Pa.), and M13 forward and reverse primers (10 µM)] were inoculated with a single transformant and heated to 95° C. for 4 minutes, followed by 25 cycles of (98° C. for 20 seconds, 60° C. for 20 seconds, 72° C. for 1 minute per kb, and ending with a final extension at 72° C. for 2 minutes. The reactions were analyzed by electrophoresis using either 1% 96-well or 1.2% 12-well agarose E-Gels containing ethidium bromide and visualized under UV light. Colonies positive for correct size inserts were cultured for plasmid DNA purification (Promega). After validation, purified plasmid DNA was subject to a second recombination reaction to recombine the insert into pEXP4-DEST expression vector (Invitrogen) using LR Clonase II enzyme mix (Invitrogen). Each reaction was incubated for 1 hour per kb of insert. All recombination reactions were transformed into Mach1 chemically competent cells with heat shock.

The resulting transformant colonies were screened with using colony PCR techniques with T7 consensus primers. For the PCR, 25 µl reactions were inoculated with a single transformant in the same master mix described above and heated to 95° C. for 4 minutes, followed by 25 cycles of 98° C. for 20 seconds, 45° C. for 20 seconds, 72° C. for 1 minute per kb, and ending with a final extension at 72° C. for 2 minutes. The reactions were analyzed by electrophoresis using either 1% 96-well or 1.2% 12-well agarose E-Gels containing ethidium bromide and visualized under UV light. Colonies (pEXP4-DEST(+) HSV-2 ORFs) positive for correct size inserts were cultured for plasmid DNA purification (Promega). The plasmid DNA of each validated pEXP4-DEST(+) HSV-2 ORF was then transformed with heat shock into Stbl2 chemically competent cells (Invitrogen) and also into Stbl2 expressing a cytoplasmic variant of listeriolysin O (Stbl2/pAC(+)cLLO). Glycerol stocks were prepared from each of the libraries and stored at −80° C.

Synthetic Generation of Clones

Three open reading frames contained introns, and could not be PCR amplified due to an inavailablility of viral mRNA. As a result, those clones were generated de novo by a contract company (DNA 2.0, Menlo Park, Calif.). In addition, a fourth clone was additionally synthesized de novo after repeated unsuccessful attempts to clone it using standard methods. The synthesized DNA fragments were received from DNA 2.0 as pDONR221 inserts after the fragments were size and sequence validated, and the inserts recombined into pEXP4-DEST as described above.

Library Sequence Validation

To verify the sequence of each cloned ORF, the entire pEXP4-DEST(+) ORFeome library was sent for single pass sequencing at Agencourt in Beverly, Mass. To prepare samples for sequencing, 200 µl media (10 g/L tryptone and 5 g/L yeast extract (both from BD), plus 5 g/L sodium chloride and 10% glycerol (both from Fisher) was aliquoted into a round bottom, 96 well plate and each well was inoculated with a single clone from glycerol stocks of the Mach1/pEXP4 (+) HSV-2 ORF library. The cultures were grown statically for approximately 8 hours at 37° C., then checked for growth and frozen at −80° C. The plate was delivered to Agencourt via a courier service and single pass sequencing was done by primer walking. Sequence data were analyzed using Vector NTI software (Invitrogen).

Library Induction 96-well deep-well plates containing were inoculated from the frozen libraries by aliquoting 500 µL of LB+100 µg/mL carbenicillin (+40 µg/mL chloramphenicol if the library contained cLLO) per well of deep-well 96-well plates, and with a 12-channel p200 pipet, gouging the tips into the glycerol stock of frozen library and transferring the slurry to the LB. Plates were covered with a gas permeable membrane and incubated overnight with shaking at 37° C. The next day, cultures were back-diluted 1:100 into new plates in 1 mL of LB containing 0.2% maltose, 100 µg/mL carbenicillin (and 40 µg/mL chloramphenicol if the library contained cLLO). Plates were covered with a gas permeable membrane and incubated with shaking until the $OD_{600}$ reached between 0.6 and 0.8. The median OD of the plate was calculated, and the average number of bacteria per well were extrapolated. Ten millimolar $MgSO_4$ was added to each well followed by λCE6 bacteriophage (Novagen, Gibbstown, N.J.) at a multiplicity of infection of twelve phage to one bacterium. Plates were gently mixed then incubated at 37° C. without shaking for 20 minutes then an additional hour and forty minutes with shaking, after which the $OD_{600}$ was measured. From the OD calculations, the number of bacteria per well were determined Bacteria were pelleted and resuspended in 0.5% paraformaldehyde per well, incubated at room temperature for 30 minutes, and then washed two times with 1×PBS. The bacteria were pelleted again, and then resuspended in RPMI containing 10% FCS, 55 µM 2-mercaptoethanol, and 1× non-essential amino acids, sodium pyruvate, and L-glutamine for a final concentration of $2×10^8$ bacteria per mL. The induced bacteria were aliquoted in 50 µL volumes into the same wells of new 96-well v-bottom plates; the plates were covered with aluminum plate sealers, and frozen at −80° C.

Example 2

Screening a Library with Human Peripheral Blood Cells to Identify Human Antigens from Herpes Simplex Virus-2

Preparation of PBMCs

Human whole blood from an HSV-2$^+$/HSV-1$^-$ patient was collected via venepuncture into eight sodium heparin CPT tubes (Becton Dickenson, Franklin Lakes, N.J.) at Bioreclamation Inc. (Hicksville, N.Y.), for a total of 64 mL. The patient was diagnosed with in 1988, with a last reported outbreak of April of 2007, and was on daily antiviral drugs. All tubes were centrifuged immediately after collection according to manufacturer's instructions, and then shipped at 4° C. overnight. Upon receipt of the tubes, the samples were acclimated to room temperature, mixed and then centrifuged again according to the manufacturer's instructions. Plasma was removed and frozen at −20° C., and the cell layer was transferred to a 50 mL centrifuge tube. The empty CPT tube was washed three times with 3 mL PBS, and the washes were pooled into the tube containing the cells. Cells were pelleted and then resuspended in degassed PBS containing 2 mM EDTA and 0.5% BSA and counted.

Cell Sorting

Specific cell populations were positively selected out of the total PBMC using magnetic beads (Miltenyi Biotec, Auburn, Calif.), following the manufacturer's instructions. $CD4^+$ T cells were sorted first, followed by $CD8^+$ T cells from the CD4 depleted fraction of cells. Finally, dendritic cells (DC) were sorted from the T cell depleted fraction. All sorted cells were stored on ice until used. A fraction of the remaining cells (T- and DC-depleted) were used to supplement the DCs for the ex vivo screen of the library (described below) and the remainder were frozen at a concentration of $10^6$ cells/mL in characterized FBS containing 10% DMSO and stored in liquid nitrogen.

Ex Vivo Library Screening

The T cells ($CD8^+$ for the cLLO-containing library and $CD4^+$ for the non-cLLO containing library) were counted and adjusted to a concentration of $5\times10^5$ cells/mL in complete medium (equal volumes of RPMI-1640 and α-MEM with glutamax containing 10% human AB serum, 55 µM 2-mercaptoethanol, and 1× each of HEPES, non-essential amino acids, penicillin/streptomycin, sodium pyruvate, and L-glutamine) containing 20 U/mL rhIL-2 and returned to ice until use.

Plates containing the induced, fixed, and frozen libraries (with or without cLLO co-expressed) were removed from the −80° C. freezer and allowed to thaw at room temperature. Freshly isolated dendritic cells were mixed with T- and DC-depleted cells for a final concentration of $2\times10^6$ cells/mL (the ratio of DC to non-DC/T cells was approximately 1:4) and 50 µL per well were loaded into round-bottom 96-well plates for a total of $1\times10^5$ APC per well. 50 µL of the thawed library was added to each well ($10^7$ bacteria per well), and the plates were incubated for 1 h at 37° C., 5% $CO_2$. Following incubation, the plates were washed three times with 1×PBS, centrifuging the plates with each wash to pellet the cells. The cells were then incubated in complete medium at 37° C., 5% $CO_2$ for an additional hour to allow antigen processing. Following the second incubation, the cells were pelleted and then fixed in 1% paraformaldehyde (PFA) for 15 minutes, after which they were washed and incubated with 120 mM lysine in PBS to remove any residual PFA.

After one more wash in PBS, the pellets were resuspended in 200 µL per well properly diluted T cells. Plates were incubated at 37° C. for 24 h, after which 150 µL cell-free supernatant was harvested into the same wells of a new, v-bottom 96-well plate and frozen at −20° C. for ELISA analysis. 150 µL fresh complete medium (no IL-2) was replaced in each well and the plates were allowed to incubate at 37° C., 5% $CO_2$ for an additional 6 days, followed by a second harvest of 150 µL cell-free supernatant for a second ELISA analysis.

Non-Specific Expansion of Sorted T Cells

Sorted T cells that weren't used in the ex vivo library screen described below were non-specifically expanded using the Miltenyi MACSiBead Particles following the recommended protocols. Briefly, $10^8$ anti-biotin MACSiBead particles were loaded with equal concentrations of biotin-conjugated CD2, CD3 and CD28-specific antibodies, and mixed with the sorted T cells in complete medium at a ratio of 0.5:1. Cells and beads were cultured at 37° C., 5% $CO_2$, at a density of $5\times10^6$ cells/mL/$cm^2$ for three days. On days three and five, the cultures were split into two equal parts and supplemented with medium containing 20 U/mL rhIL-2. On day seven, the cells were used to screen the HSV-2 library, as described below.

Library Screening with Non-Specifically Expanded T Cells

The library screen was set up as described for the ex vivo screen, with the exceptions that medium alone or 5 µg/mL PHA (Sigma) were added to T cells in separate wells as negative and positive controls, respectively; the antigen presenting cells were T- and DC-depleted cells that had been frozen at −80° C. and thawed just prior to the assay; and the supernatant from the assay was harvested and frozen only at 24 h.

ELISA Assay for IFNγ Determination

IFNγ levels in the supernatants were assayed using the OptEIA IFNγ ELISA kit from BD Biosciences (San Jose, Calif.) following the manufacturer's instructions with the exception that all volumes were halved. Supernatants were thawed at room temperature and diluted 1:5 and 1:20 in PBS containing 10% FCS. Samples that were positive in the ELISA were rescreened in a second ELISA assay to verify the results.

FIG. 1 shows results for $CD8^+$ T cells freshly isolated from an HSV-2 infected patient. Cells were cocultured with autologous antigen presenting cells that had been pulsed with *E. coli* expressing cytoplasmic LLO. Cell free supernatants were harvested after 7 days of culture. Each bar represents IFNγ levels secreted by T cells exposed to antigen presenting cells pulsed with a single viral clone. Black bars represent antigens that had been previously identified by others using other methods. Six of the clones represented by white bars have no known function, and likely would not have been identified by conventional methods of antigen discovery. These data show that methods described herein successfully identify known human antigens to an infectious agent, and can be used to reveal novel antigens.

Example 3

High-Throughput Library Validation of Heterologous Polypeptide Expression and MHC Presentation In order to perform high-throughput determination of library protein expression and delivery to either the MHC class I or MHC class II presentation pathways, a C-terminal tag that contains both $CD4^+$ and $CD8^+$ T cell epitopes from chicken ovalbumin ($OVA_{247-265}$ (PDEVSGLEQLESIIN-FEKL; SEQ ID NO:9) and $OVA_{258-265}$ (SIINFEKL; SEQ ID NO:10) respectfully, corresponding to positions in the amino acid sequence found in GenBank® under Acc. No. NP_990483) was inserted into pDEST17 to create pDESTSL4.8. When PCR products containing ORFs (e.g., ORFs from an infectious agent of interest) are recombined into pDESTSL4.8 using the Gateway recombination system, the tag is fused to each expressed ORF on the C-terminus. This tag can be used to determine whether each protein was expressed to full length and delivered to the proper MHC presentation pathway.

For evaluating MHC class I presentation, the proteins are co-expressed with cLLO in *E. coli*. The bacteria are then pulsed onto bone marrow macrophages (BMM) derived from an H2$^b$ haplotype mouse. The cLLO facilitates delivery of each expressed ORF along with the C-terminal tag to the MHC class I presentation pathway in the BMM. If the full length of each ORF is expressed and properly delivered to the MHC class I pathway, the OVA$_{258-265}$ peptide is processed and presented on the MHC class I molecules, which are H2-K$^b$ molecules, in the BMM cells. Presentation of this peptide can be detected through the use of B3Z T hybridoma cells, which activate upon recognizing this specific OVA peptide-MHC complex. Activated B3Z T cells produce β-galactosidase, which can be detected through the use of colorimetric β-galactosidase substrates such as chlorophenyl red β-D galactopyranoside (CPRG). CPRG changes from a yellow to a dark magenta color when cleaved by β-galactosidase, which indicates the ORF is expressed and processed properly.

For MHC class II presentation, the proteins are induced in *E. coli* in the absence of cLLO. The bacteria are then pulsed onto BMM derived from an H2$^k$ haplotype mouse. The expressed protein remains in the vacuole and is delivered to the MHC class II pathway along with the C-terminal tag. The OVA$_{247-265}$ tag is processed and presented on H2-A$^k$ molecules on the surface of the cell which are recognized by KZO T hybridoma cells. KZO cells upregulate β-galactosidase in response to the peptide-MHC complex which is again measured with CPRG detection. In this manner, protein expression and both MHC class I and class II presentation can be confirmed prior to screening the library with pathogen-specific T cells.

EQUIVALENTS

Those skilled in the art will recognize, or be able to ascertain using no more than routine experimentation, many equivalents to the specific embodiments of the invention described herein. The scope of the present invention is not intended to be limited to the above Description. Alternative methods and materials and additional applications will be apparent to one of skill in the art, and are intended to be included within the following claims:

---

We claim:

1. A method of evaluating an immune response of a human subject, the method comprising:
   (a) providing a library comprising bacterial cells, wherein each bacterial cell of the library comprises a heterologous polypeptide;
   (b) contacting the bacterial cells with a first plurality of human cells which includes non-professional human antigen presenting cells that internalize the bacterial cells;
   (c) contacting the first plurality of human cells with a second plurality of human cells from the human subject which comprises human lymphocytes that are not selected for specifically responding to the antigen, under conditions in which lymphocytes are stimulated by polypeptides presented by the first plurality of human cells; and
   (d) determining whether a lymphocyte of the second plurality of human cells is stimulated by a heterologous polypeptide presented by a cell of the first plurality of human cells, thereby evaluating an immune response of the human subject.

2. The method of claim 1, wherein the first plurality of human cells is isolated from the human subject.

3. The method of claim 1, wherein the heterologous polypeptides comprise polypeptides encoded by an infectious agent, and wherein stimulation of a lymphocyte of the second plurality of human cells by a polypeptide encoded by the infectious agent presented by a cell of the first plurality of human cells indicates that the human subject has an immune response to the infectious agent.

4. The method of claim 1, wherein the heterologous polypeptides comprise polypeptides differentially expressed in cancer or a tumor cell.

5. The method of claim 4, wherein stimulation of a lymphocyte of the second plurality of human cells by a polypeptide differentially expressed in cancer or a tumor cell presented by a cell of the first plurality of human cells indicates that the human subject has an immune response to the polypeptide differentially expressed in cancer or a tumor cell.

6. The method of claim 1, wherein the heterologous polypeptides comprise polypeptides from a target cell of the human subject.

7. The method of claim 6, wherein stimulation of a lymphocyte of the second plurality of human cells by a polypeptide from a target cell of the human subject presented by a cell of the first plurality of human cells indicates that the human subject has an immune response to the target cell of the human subject.

8. The method of claim 3, wherein stimulation of a lymphocyte of the second plurality of human cells by a polypeptide encoded by the infectious agent presented by a cell of the first plurality of human cells indicates that the human subject has been exposed to the infectious agent.

9. The method of claim 3, wherein the bacterial cells further comprise a cytolysin polypeptide.

10. The method of claim 9, wherein the cytolysin polypeptide is listeriolysin O (LLO).

11. The method of claim 3, wherein the first plurality of human cells is provided in an array, and wherein cells in each location of the array are contacted with a set of bacterial cells, each set comprising a different heterologous polypeptide.

12. The method of claim 3, wherein the infectious agent is an intracellular infectious agent.

13. The method of claim 3, wherein the infectious agent is an extracellular infectious agent.

14. The method of claim 3, wherein the infectious agent is a virus.

15. The method of claim 3, wherein the infectious agent is a bacterium.

16. The method of claim 3, wherein the infectious agent is a fungus, protozoan, or helminth.

17. The method of claim 1, wherein the first and second plurality of human cells comprise cells from peripheral blood.

18. The method of claim 1, wherein the first plurality of human cells comprises dendritic cells.

19. The method of claim 17, wherein the first plurality of human cells comprises peripheral blood cells from which T cells and dendritic cells have been depleted.

20. The method of claim 17, wherein the first plurality of human cells comprises dendritic cells and peripheral blood cells from which T cells and dendritic cells have been depleted.

21. The method of claim 20, wherein the first plurality of human cells comprises dendritic cells and peripheral blood cells from which T cells and dendritic cells have been depleted at a ratio of about 1:2, 1:3, 1:4, or 1:5.

22. The method of claim 3, further comprising identifying a polypeptide that stimulates a lymphocyte of the second plurality of human cells as an antigen of the infectious agent.

23. The method of claim 22, further comprising formulating the antigen or a nucleic acid encoding the antigen as an immunogenic composition.

* * * * *

SEQUENCE LISTING

<160> NUMBER OF SEQ ID NOS: 10

<210> SEQ ID NO 1
<211> LENGTH: 529
<212> TYPE: PRT
<213> ORGANISM: Listeria monocytogenes

<400> SEQUENCE: 1

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
```

```
            225                 230                 235                 240
        Glu Gly Lys Met Gln Glu Val Ile Ser Phe Lys Gln Ile Tyr Tyr
                        245                 250                 255

Asn Val Asn Val Asn Glu Pro Thr Arg Pro Ser Arg Phe Phe Gly Lys
                        260                 265                 270

Ala Val Thr Lys Glu Gln Leu Gln Ala Leu Gly Val Asn Ala Glu Asn
                        275                 280                 285

Pro Pro Ala Tyr Ile Ser Ser Val Ala Tyr Gly Arg Gln Val Tyr Leu
                        290                 295                 300

Lys Leu Ser Thr Asn Ser His Ser Thr Lys Val Lys Ala Ala Phe Asp
        305                 310                 315                 320

Ala Ala Val Ser Gly Lys Ser Val Ser Gly Asp Val Glu Leu Thr Asn
                        325                 330                 335

Ile Ile Lys Asn Ser Ser Phe Lys Ala Val Ile Tyr Gly Gly Ser Ala
                        340                 345                 350

Lys Asp Glu Val Gln Ile Ile Asp Gly Asn Leu Gly Asp Leu Arg Asp
                        355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
        385                 390                 395                 400

Lys Asn Asn Ser Glu Tyr Ile Glu Thr Thr Ser Lys Ala Tyr Thr Asp
                        405                 410                 415

Gly Lys Ile Asn Ile Asp His Ser Gly Gly Tyr Val Ala Gln Phe Asn
                        420                 425                 430

Ile Ser Trp Asp Glu Val Asn Tyr Asp Pro Glu Gly Asn Glu Ile Val
                        435                 440                 445

Gln His Lys Asn Trp Ser Glu Asn Asn Lys Ser Lys Leu Ala His Phe
                        450                 455                 460

Thr Ser Ser Ile Tyr Leu Pro Gly Asn Ala Arg Asn Ile Asn Val Tyr
        465                 470                 475                 480

Ala Lys Glu Cys Thr Gly Leu Ala Trp Glu Trp Trp Arg Thr Val Ile
                        485                 490                 495

Asp Asp Arg Asn Leu Pro Leu Val Lys Asn Arg Asn Ile Ser Ile Trp
                        500                 505                 510

Gly Thr Thr Leu Tyr Pro Lys Tyr Ser Asn Lys Val Asp Asn Pro Ile
                        515                 520                 525

Glu

<210> SEQ ID NO 2
<211> LENGTH: 506
<212> TYPE: PRT
<213> ORGANISM: Listeria monocytogenes

<400> SEQUENCE: 2

Met Lys Asp Ala Ser Ala Phe Asn Lys Glu Asn Ser Ile Ser Ser Met
        1               5                   10                  15

Ala Pro Pro Ala Ser Pro Ala Ser Pro Lys Thr Pro Ile Glu Lys
                        20                  25                  30

Lys His Ala Asp Glu Ile Asp Lys Tyr Ile Gln Gly Leu Asp Tyr Asn
                        35                  40                  45

Lys Asn Asn Val Leu Val Tyr His Gly Asp Ala Val Thr Asn Val Pro
                        50                  55                  60

Pro Arg Lys Gly Tyr Lys Asp Gly Asn Glu Tyr Ile Val Val Glu Lys
```

```
             65                  70                  75                  80
Lys Lys Lys Ser Ile Asn Gln Asn Asn Ala Asp Ile Gln Val Val Asn
                 85                  90                  95

Ala Ile Ser Ser Leu Thr Tyr Pro Gly Ala Leu Val Lys Ala Asn Ser
                100                 105                 110

Glu Leu Val Glu Asn Gln Pro Asp Val Leu Pro Val Lys Arg Asp Ser
                115                 120                 125

Leu Thr Leu Ser Ile Asp Leu Pro Gly Met Thr Asn Gln Asp Asn Lys
    130                 135                 140

Ile Val Val Lys Asn Ala Thr Lys Ser Asn Val Asn Asn Ala Val Asn
145                 150                 155                 160

Thr Leu Val Glu Arg Trp Asn Glu Lys Tyr Ala Gln Ala Tyr Pro Asn
                165                 170                 175

Val Ser Ala Lys Ile Asp Tyr Asp Glu Met Ala Tyr Ser Glu Ser
                180                 185                 190

Gln Leu Ile Ala Lys Phe Gly Thr Ala Phe Lys Ala Val Asn Asn Ser
                195                 200                 205

Leu Asn Val Asn Phe Gly Ala Ile Ser Glu Gly Lys Met Gln Glu Glu
    210                 215                 220

Val Ile Ser Phe Lys Gln Ile Tyr Tyr Asn Val Asn Val Asn Glu Pro
225                 230                 235                 240

Thr Arg Pro Ser Arg Phe Phe Gly Lys Ala Val Thr Lys Glu Gln Leu
                245                 250                 255

Gln Ala Leu Gly Val Asn Ala Glu Asn Pro Pro Ala Tyr Ile Ser Ser
                260                 265                 270

Val Ala Tyr Gly Arg Gln Val Tyr Leu Lys Leu Ser Thr Asn Ser His
                275                 280                 285

Ser Thr Lys Val Lys Ala Ala Phe Asp Ala Ala Val Ser Gly Lys Ser
    290                 295                 300

Val Ser Gly Asp Val Glu Leu Thr Asn Ile Ile Lys Asn Ser Ser Phe
305                 310                 315                 320

Lys Ala Val Ile Tyr Gly Gly Ser Ala Lys Asp Glu Val Gln Ile Ile
                325                 330                 335

Asp Gly Asn Leu Gly Asp Leu Arg Asp Ile Leu Lys Lys Gly Ala Thr
                340                 345                 350

Phe Asn Arg Glu Thr Pro Gly Val Pro Ile Ala Tyr Thr Thr Asn Phe
                355                 360                 365

Leu Lys Asp Asn Glu Leu Ala Val Ile Lys Asn Asn Ser Glu Tyr Ile
    370                 375                 380

Glu Thr Thr Ser Lys Ala Tyr Thr Asp Gly Lys Ile Asn Ile Asp His
385                 390                 395                 400

Ser Gly Gly Tyr Val Ala Gln Phe Asn Ile Ser Trp Asp Glu Val Asn
                405                 410                 415

Tyr Asp Pro Glu Gly Asn Glu Ile Val Gln His Lys Asn Trp Ser Glu
                420                 425                 430

Asn Asn Lys Ser Lys Leu Ala His Phe Thr Ser Ser Ile Tyr Leu Pro
                435                 440                 445

Gly Asn Ala Arg Asn Ile Asn Val Tyr Ala Lys Glu Cys Thr Gly Leu
    450                 455                 460

Ala Trp Glu Trp Trp Arg Thr Val Ile Asp Asp Arg Asn Leu Pro Leu
465                 470                 475                 480

Val Lys Asn Arg Asn Ile Ser Ile Trp Gly Thr Thr Leu Tyr Pro Lys
                485                 490                 495
```

Tyr Ser Asn Lys Val Asp Asn Pro Ile Glu
            500                 505

<210> SEQ ID NO 3
<211> LENGTH: 571
<212> TYPE: PRT
<213> ORGANISM: Streptococcus pyogenes

<400> SEQUENCE: 3

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Ser Glu
        35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Asp Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala

```
                355                 360                 365
Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 4
<211> LENGTH: 500
<212> TYPE: PRT
<213> ORGANISM: Clostridium perfringens

<400> SEQUENCE: 4

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160
```

Leu Val Ser Lys Trp Asn Glu Lys Tyr Ser Thr His Thr Leu Pro
            165                 170                 175

Ala Arg Thr Gln Tyr Ser Glu Ser Met Val Tyr Ser Lys Ser Gln Ile
        180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
210                 215                 220

Ala Tyr Lys Gln Ile Phe Tyr Thr Val Ser Ala Asp Leu Pro Lys Asn
225                 230                 235                 240

Pro Ser Asp Leu Phe Asp Ser Val Thr Phe Asn Asp Leu Lys Gln
            245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
            275                 280                 285

Asp Val Gln Ala Ala Phe Lys Ala Leu Ile Lys Asn Thr Asp Ile Lys
            290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
            325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
            355                 360                 365

Asp Asn Ser Val Ala Ala Val His Asn Lys Thr Asp Tyr Ile Glu Thr
            370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
            405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
            435                 440                 445

Ala Arg Asn Ile Arg Ile Lys Ala Arg Glu Cys Thr Gly Leu Ala Trp
            450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
acaaaaaagc aggctgc                                                17

```
<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
acaagaaagc tgggtag                                                    17

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gggacaagtt tgtacaaaaa agcaggctgc                                      30

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ggggaccact ttgtacaaga aagctgggta g                                    31

<210> SEQ ID NO 9
<211> LENGTH: 19
<212> TYPE: PRT
<213> ORGANISM: Gallus gallus

<400> SEQUENCE: 9

Pro Asp Glu Val Ser Gly Leu Glu Gln Leu Glu Ser Ile Ile Asn Phe
1               5                   10                  15

Glu Lys Leu

<210> SEQ ID NO 10
<211> LENGTH: 8
<212> TYPE: PRT
<213> ORGANISM: Gallus gallus

<400> SEQUENCE: 10

Ser Ile Ile Asn Phe Glu Lys Leu
1               5
```